(12) United States Patent
DeBaun et al.

(10) Patent No.: US 10,543,247 B2
(45) Date of Patent: Jan. 28, 2020

(54) ALOE PREPARATION FOR SKIN ENHANCEMENT

(75) Inventors: Denise DeBaun, New York, NY (US); David Stanley Pasco, Oxford, MS (US); Nirmal Derek Ceri Pugh, Oxford, MS (US); Alex Pashkowsky, New York, NY (US); Alvin Needleman, Las Vegas, NV (US)

(73) Assignees: Woodcliff Skincare Solutions, Inc., Edison, NJ (US); University of Mississippi, University, MS (US)

( * ) Notice: Subject to any disclaimer, the term of this patent is extended or adjusted under 35 U.S.C. 154(b) by 1167 days.

(21) Appl. No.: 12/599,532

(22) PCT Filed: May 9, 2008

(86) PCT No.: PCT/US2008/006089
§ 371 (c)(1),
(2), (4) Date: Nov. 10, 2009

(87) PCT Pub. No.: WO2008/140820
PCT Pub. Date: Nov. 20, 2008

(65) Prior Publication Data
US 2010/0255130 A1  Oct. 7, 2010

Related U.S. Application Data

(60) Provisional application No. 60/928,924, filed on May 11, 2007.

(51) Int. Cl.
*A61K 36/886* (2006.01)

(52) U.S. Cl.
CPC ................ *A61K 36/886* (2013.01)

(58) Field of Classification Search
None
See application file for complete search history.

(56) References Cited

U.S. PATENT DOCUMENTS

| | | |
|---|---|---|
| 3,103,466 A | 9/1963 | Farkas |
| 3,362,951 A | 1/1968 | Farkas |
| 4,707,354 A * | 11/1987 | Garlen .............. A61K 8/35 424/47 |
| 4,735,935 A | 4/1988 | McAnalley |
| 4,851,224 A | 7/1989 | McAnalley |
| 4,861,761 A | 8/1989 | Madis et al. |
| 4,917,890 A | 4/1990 | McAnalley |
| 4,957,907 A | 9/1990 | McAnalley |
| 4,959,214 A | 9/1990 | McAnalley |
| 4,966,892 A | 10/1990 | McAnalley |
| 5,106,616 A | 4/1992 | McAnalley et al. |
| 5,118,673 A | 6/1992 | Carpenter et al. |
| 5,284,833 A | 2/1994 | McAnalley et al. |
| 5,308,838 A | 5/1994 | McAnalley et al. |
| 5,409,703 A | 4/1995 | McAnalley et al. |
| 5,441,943 A | 8/1995 | McAnalley et al. |
| 5,443,830 A | 8/1995 | Moore et al. |
| 5,468,737 A | 11/1995 | McAnalley et al. |
| 5,512,488 A | 4/1996 | Eberendu et al. |
| 5,587,364 A | 12/1996 | McAnalley et al. |
| 5,703,060 A | 12/1997 | McAnalley et al. |
| 5,760,102 A | 6/1998 | Hall et al. |
| 5,773,425 A | 6/1998 | McAnalley et al. |
| 5,780,453 A | 7/1998 | McAnalley et al. |
| 5,786,342 A | 7/1998 | Carpenter et al. |
| 5,824,659 A | 10/1998 | Strickland et al. |
| 5,902,796 A | 5/1999 | Shand et al. |
| 5,925,357 A | 7/1999 | Cerqueira et al. |
| 5,929,051 A | 7/1999 | Ni et al. |
| 5,972,892 A | 10/1999 | De Lacharriere et al. |
| 6,106,849 A | 8/2000 | Malkan et al. |
| 6,133,440 A | 10/2000 | Qiu et al. |
| 6,274,548 B1 | 8/2001 | Ni et al. |
| 6,313,103 B1 | 11/2001 | Ni et al. |
| 6,777,000 B2 | 8/2004 | Ni et al. |
| 6,929,807 B1 | 8/2005 | McAnalley et al. |
| 7,022,683 B1 | 4/2006 | Ni et al. |
| 7,157,431 B2 | 1/2007 | McAnalley et al. |
| 7,196,064 B2 | 3/2007 | McAnalley et al. |
| 7,196,072 B2 | 3/2007 | Pasco et al. |
| 7,199,104 B2 | 4/2007 | McAnalley et al. |
| 7,202,220 B2 | 4/2007 | McAnalley et al. |

(Continued)

FOREIGN PATENT DOCUMENTS

| | | | | |
|---|---|---|---|---|
| CN | 1159923 A | * | 9/1997 | .......... A61K 31/715 |
| CN | 1201661 A | * | 12/1998 | ............. A61K 31/70 |

(Continued)

OTHER PUBLICATIONS

Barret, S. "Homeopathy: The Ultimate Fake". Internet archive date: Oct. 12, 2002 [Retrieved from the internet on: Jan. 13, 2017]. Retrieved from the Internet: <URL: http://web.archive.org/web/20021012082916/http://www.quackwatch.org/01QuackeryRelatedTopics/homeo.html>.*
Remington's. "Remington's Pharmaceutical Science 17th Edition". Gannaro, A (Ed.). pp. 1480, 1513. (Year: 1985).*
International Search Report, PCT/US2008/06089.
Ukai et al., [Journal of Pharmacobio-Dynamics, 6(12):983-990 (1983).
Saeki et al., Japanese Journal of Pharmacology, 24(1):109-118 (1974).
Arita et al., Journal of Biochemistry, 76(4):861-869 (1974).
Rocha et al., Biochemical Pharmacology, 18:1285-1295 (1969).
Yagi et al., [Planta Medica, 31(1):17-20 (1977).
Ovodova [Khim, Prior, Soedin, 11(1):325-331 (1975).

(Continued)

*Primary Examiner* — Amy L Clark
(74) *Attorney, Agent, or Firm* — Lerner, David, Littenberg, Krumholz & Mentlik, LLP

(57) ABSTRACT

Methods for providing skin enhancement and pain relief to an individual in need of treatment by administering to such an individual an effective amount of an immunostimulatory *Aloe vera* derived composition. Oral and topical methods and compositions are provided. *Aloe vera* derived immunostimulatory compositions and methods of producing such compositions are provided.

46 Claims, 18 Drawing Sheets

(56) References Cited

U.S. PATENT DOCUMENTS

| | | |
|---|---|---|
| 7,494,669 B2 | 2/2009 | Ni et al. |
| 7,691,986 B2 | 4/2010 | Ni et al. |
| 7,705,135 B2 | 4/2010 | Ni et al. |
| 7,767,655 B2 | 8/2010 | Pasco et al. |
| 2002/0119941 A1 | 8/2002 | Ni et al. |
| 2003/0072770 A1 | 4/2003 | McAnalley et al. |
| 2003/0175370 A1 | 9/2003 | Yates et al. |
| 2003/0220485 A1 | 11/2003 | Ni et al. |
| 2004/0038931 A1 | 2/2004 | Elsobly et al. |
| 2004/0170706 A1 | 9/2004 | McAnalley et al. |
| 2004/0171583 A1 | 9/2004 | McAnalley et al. |
| 2005/0008713 A1 | 1/2005 | McAnalley et al. |
| 2005/0037096 A1 | 2/2005 | Yates et al. |
| 2005/0048143 A1 | 3/2005 | McAnalley et al. |
| 2005/0084534 A1 | 4/2005 | Ni et al. |
| 2005/0214413 A1 | 9/2005 | McAnalley et al. |
| 2006/0040003 A1 | 2/2006 | Needleman et al. |
| 2006/0084629 A1 | 4/2006 | Needleman et al. |
| 2006/0211653 A1 | 9/2006 | Ni et al. |
| 2007/0149478 A1 | 6/2007 | McAnalley et al. |
| 2007/0190209 A1 | 8/2007 | Sinnott |
| 2007/0286914 A1 | 12/2007 | Pasco et al. |
| 2008/0286252 A1 | 11/2008 | Sinnott |
| 2009/0004220 A1 | 1/2009 | McAnalley et al. |

FOREIGN PATENT DOCUMENTS

| | | | |
|---|---|---|---|
| CN | 1370587 A | 9/2002 | |
| EP | 0328775 A1 | 8/1989 | |
| EP | 0611304 A1 | 8/1994 | |
| EP | 0871460 A1 | 10/1998 | |
| EP | 0884994 A1 | 12/1998 | |
| EP | 0966294 A1 | 12/1999 | |
| EP | 1607407 A2 | 12/2005 | |
| JP | 03053868 A * | 3/1991 | |
| JP | 03-501624 | 4/1991 | |
| JP | 2001-520019 | 10/2001 | |
| JP | 2003252719 A * | 9/2003 | |
| WO | 8700052 A1 | 1/1987 | |
| WO | 8906539 A1 | 7/1989 | |
| WO | 9001253 A1 | 2/1990 | |
| WO | 9308810 A1 | 5/1993 | |
| WO | 9510199 A1 | 4/1995 | |
| WO | 9710834 A1 | 3/1997 | |
| WO | 9729731 A1 | 8/1997 | |
| WO | 9841221 A1 | 9/1998 | |
| WO | 9919505 A1 | 4/1999 | |
| WO | 9958575 A1 | 11/1999 | |
| WO | 0005257 A1 | 2/2000 | |
| WO | 0041541 A2 | 7/2000 | |
| WO | 02/03999 A1 | 1/2002 | |
| WO | WO-0203999 A1 * | 1/2002 | A61K 31/715 |
| WO | 02067897 A2 | 9/2002 | |
| WO | 03057893 A1 | 7/2003 | |
| WO | 03075891 A1 | 9/2003 | |

OTHER PUBLICATIONS

Rowe, J. Am. Pharm. Assoc., 29:348-350 (1940).
Lushbaugh et al., Cancer, 6:690-698 (1953).
Ashley et al., Plast. Reconstr. Surg., 20:383-396 (1957).
Rodriguez-Bigas et al., J. Plast. Reconstr. Surg., 81:386-389(1988).
El Zawahly et al., Int. J. Dermatol., 12:68-73 (1973).
Solar, Arch. Inst. Pasteur Madagascar, 47:9-39 (1979).
Stepanova, Fiziol. Akt. Veshchestva, 9:94-97 (1977).
Waller et al., Aloes: The Genus *ALoe*, 2004; Chapter 8, pp. 139-205.
Tizard and Ramamoorthy, Aloes: The Genus *Aloe*, 2004; Chapter 13, pp. 311-332.
Ni Y, et al, International Immunopharmacology, 2004, 4: 1745-1755.
Merkle and Poppe (1994) Methods Enzymol. 230:1-15.
York, et al. (1985) Methods Enzymol. 118:3-40.
Barel, Courage and Clarys, Handbook of Non-Invasive Methods and the Skin, Serup and Jemec, eds. 1995.
Blichman and Serup, Acta Derm Venereol, 1988.
Cua, Maibach and Wilhelm, Dermatologica Research, 1990.
Dobrev, Sixth Congress of Dermatology and Venerology, Pleve, Bulgaria, May 11-13, 1995.
Elsner P, et al., "Mechanical properties of human forearm and vulvar skin", Br. J. Dermatol. May 1990; 122(5):607-14.
Frankowski, Chen and Huth, Photonics West Annual Symposium, Electronics Imaging 2000, San Jose, Jan. 23-28, 2000.
Fiorentini, Becheroni, Iorio. Int. J. Cosmet. Sci. 26-29. 1988.
Friedman, Skover, Payonk and Geronemus, Seminars in Cutaneous Medicine and Surger, 200, 21 (4):266-273.
Krushe and Worre, Archives of Dermatologica Research. 287-293, 1995.
Morganti, Randazzo and Cardillo. Appl. Cosmet. 10 12, 1986.
Randeau, Kurdian, Sirvent, Closs and Girard, Cosmetics and Toiletries Manufacture Worldwide 2002.
Grindlay, D. Reynolds, T., J. Ethnopharmcol. 1986, 16(2-3), 117-151.
Joshi, S. P., J. Med. Aromat. Plant Sci. 1998, 20(3), 768-773.
Old, Scientific American, 258(5):59-60, 69-75 (1988).
Pal et al., Intervirol. 30:27-35 (1989).
Simon, Arzliche Kosmetologie, 256-259, 1984.
Ezendam and van Loveren, Nutr Rev., 2006, 64: 1-14.
Rovatti et al., Industrial Medicine and Surgery, 364-368 (1959).
Payne, Thesis submitted to Faculty of Baylor University, Waco, Tex., MS Degree (1970).
Pugh et al, J. Agric. Food Chem, 49; 1030-1034 (2001).
Rubel, Cosmetics & Toiletries, 98; 109-114 (1983).
Gruters et al., Nature, 330; 74-77 (1987).
Shanahan. R.W., et al, Parameters for Assessing the Efficacy of Skin Care Products. Drug & Cosmetic Industry, 140, No. 1, 42-48, 1987.
International Search Report, PCT/US01/21596, dated Nov. 5, 2001.
European Office Action for Application No. 08754396.3 dated Sep. 27, 2013.
Canadian Office Action for Application No. 2,687,063 dated Aug. 9, 2012.
Canadian Office Action for Application No. 2,687,063 dated Jul. 8, 2013.
Japanese Office Action for Application No. 2010-508397 dated Mar. 1, 2013.
Chinese Office Action for Application No. 201210541335.5 dated Nov. 21, 2013.
European Office Action for Application No. 08 754 396.3 dated Jun. 28, 2012.
Japanese Office Action for Application No. 2010-508397 dated Apr. 25, 2014.
Johnson, A.G., "Molecular adjuvants and immunomodulators: new approaches to immunization", Clinical Microbiology Reviews, Jul. 1994, vol. 7, No. 3, pp. 277-289.
Li Wu, et.al., Progress on the study of pharmacological effects of Aloe polysaccharide, Chinese Journal of Traditional Medical Science and Technology, 2005, 12(3), pp. 200-201 (Google machine translation enclosed).
Canadian Office Action for Application No. 2,687,063 dated Jun. 5, 2014.
European Examination Report for Application No. 08754396.3 dated Jul. 29, 2014.
Chinese Office Action for Application No. 2012105413335.5 dated Aug. 12, 2014.
Supplementary European Search Report, EP 08754396, dated Feb. 2, 2011.
Peng S Y et al: "Decreased mortality of Norman murine sarcoma in mice treated with the immunomodulator, Acemannan", Molecular Biotherapy, Butterworth, Stoneham, MA, US, vol. 3, No. 2, Jun. 1, 1991 (Jun. 1, 1991), pp. 79-87, XP009142243.
Reynolds T et al: "Aloe vera leaf gel: A review update", Journal of Ethnopharmacology, Elsevier Scientific Publishers Ltd, IE, vol. 68, No. 1-3, Dec. 15, 1999 (Dec. 15, 1999), pp. 3-37, XP002538848.
Database WPI Week 200534 Thomson Scientific, London, GB; AN 2005-333858, XP002613844, & ZA 200402034 A (Fransettie Pharm CC) Nov. 24, 2004 (Nov. 24, 2004 ).

(56) References Cited

OTHER PUBLICATIONS

Database WPI Week 200307 Thomson Scientific, London, GB; AN 2003-068686 XP002613845, & CN 1 370 587 A (Wang S) Sep. 25, 2002 (Sep. 25, 2002).
Office Action from Chinese Application No. 20088023047.2 dated Mar. 23, 2011.
Duan et al., Journal of Neijiang Teachers College, 19(6); 66-67 (2004). (English translation of abstract only).
Third Party Observation filed in Canadian Patent Application No. 2687063, dated Apr. 13, 2011.
Manthana Bhairava; AnandIlkandIll:J—Edited with Tamil translation by S.V, Radhakrishna Sastri, T.M.S.S.M. Library. Tanjore. Madras, Edn. 1st 1952 p. 228 Formulation ID: RS 13 / 310D formulation Name: Kumari Kalpah.
Abu Bakr Mohammad.Bin Zakariyya Al-Razi; Kitaab-al-Haawi-fil-Tibb, vol. IX (9th century AD), DayeTah-al-Me'aaTif Usmania, Hyderabad, (First Edition) 1960 AD p. 194 Formulation ID: AA9/ 1202 Formulation Name: Sibr.
Mohammad Azam Khan; Muheet-e-Azam vol. III(19th century AD), Matba Nizami, Kanpur, 1887 AD p. 165 Formulation ID: JA 7/3191 Formulation Name: Tila Barae Humrah Wa Namlah.
Mohammad Najmul Ghani Khan; Khazaain-al-Advia, vol. 1 (20th century AD), Nadccm Yunus Printer I Sheikh Mohd Basheer & Sons. Lahore, 1911 AD p. 669 Formulation ID: NA21275Z29 Formulation Name: Zimaad Bara-e-Wasec.
Ali Ibn-e-Abbllas Majoosi; Kaamil-al-Sena'ah, Part II (10th century ADJ. Central Council for Research in Unani Medicine, 61-65 Institutional Area, Janak Puri, New Delhi-58, 2005 AD p. 123 Formulation ID: AH3/804C Formulation Name: Dawa Baraae Indemaal-e-Qurooh.
Manthana Bhairava; Anandakanda—. Edited with Tamil translation by S.V. Radhakrishna Sastri, T.M,S.S.M. Library, Tanjore, Madras, Edn. 1st 1952 p. 227 Formulation ID: RS 13/31 OA Formulation Name: Kumari Kalpah.
Abu Bakr Mohammad.Bin Zakariyya Al-Razi; Kitaab-al-Haawi-fil-Tibb. vol. XI (9th century AD). Dayerah-al-Ma'aarif Usmania, Hyderabad, (First Edition) 1962 AD p. 129 Formulation ID: AA11/ 494 Formulation Name: Tila Baraa-e-Waja-ul-Rukbah.
Mohammad Akmal Khan; Qaraabaadeen Azam wa Akmal (20th century AD), Matha Siddiqi, Delhi / Matba Mustafai, Delhi, 1909 AD p. 390 Formulation ID: AH5 / 419 Formulation Name: Zaroor-e-kundur Baraai Sartaan.
Mohammad Azam Khan; Ikseer Azam, vol. IV (19th century AD), Matba Nizami, Kanpur, 1872 AD p. 312 Formulation ID: 8A4/ 1861H Formulation Name: Nuskha-e-tila.
Mohammad Najmul Khan Khazaain-al-Advia, vol. I (20th century AD), Ghani Nadeem Yunus Printer / Sheikh Mohd Basheer & Sons, Lahore, 1911 AD, Formulation ID: NA2/275Z23, p. 669, Formulation Name: Zimaad Barra-e-Amraaz-e-Jild.
Abu Mohammad Bin Zakariyya Al-Razi Bakr Kitaab-al-Haawi-fil-Tibb, vol. XXI part I (9th century AD), Dayerah-al-Maaarif Usmania, Hedrabad, (First Edition) 1968 AD., p. 143, AA21/91 E, Dawa-e-sibr Aakhar.
Mohamaad Khan, Azam Ikseer Azam, vol. IV (19th century AD), Marba Nizami, Kanpur, 1872 AD, p. 107, BA4/835C, Suskha-e-hab.
Mohammad Najmul Khan Khazaain-al-Advia, vol. I (20th century AD), Ghani Nadeem Yunus Printer / Sheikh Mohd Basheer & Sons, Lahore, 1911 AD, p. 665, NA2/275C, Marham-e-elwa.
Mohamaad Khan, Azam Ikseer Azam, vol. IV (19th century AD), Marba Nizami, Kanpur, 1872 AD, p. 331, BA4/1860A, Nuskha-e-qairooti.
Abu Mohammad Bin Zakariyya Al-Razi Bakr Kitaab-al-Haawi-fil-Tibb, vol. XI part I (9th century AD), Dayerah-al-Maaarif Usmania, Hedrabad, (First Edition) 1968 AD., p. 129, AA11/494, Tila Baraa-e-Waju-ul-Rukbah.
Office Action from Canadian Application No. 2687063 dated Jun. 1, 2011.

\* cited by examiner

FIG. 1

Glycosyl Composition Analysis

| Sample | Glycosyl Residue | Mass (μg) | Mole %[1] |
|---|---|---|---|
| Aloe 056 | | | |
| | Ribose (Rib) | 0.6 | 1.5 |
| | Rhamnose (Rha) | 0.6 | 1.4 |
| | Fucose (Fuc) | 0.6 | 1.1 |
| | Xylose (Xyl) | 0.6 | 1.6 |
| | Arabinose (Ara) | 3.5 | 9.5 |
| | Galacturonic Acid (GalUA) | 3.7 | 7.9 |
| | Mannose (Man) | 2.9 | 6.6 |
| | Galactose (Gal) | 4.1 | 9.2 |
| | Glucose (Glc) | 26.8 | 61.1 |
| | Octadecadienoic Acid | + | + |
| | Octadecenoic Acid | + | + |
| | Octadecanoic Acid | + | + |
| | Hexadecanoic Acid | + | + |
| | | | 100.0 |
| | Sum | 43.2 | 0 |

[1] Values are expressed as mole percent of total carbohydrate. The total percent carbohydrate is calculated to be 8.6%.
n.d. = none detected

FIG. 2

SKIN ELASTICITY (Pinch Test)

Summary: There was a significant reduction in rebound time at both the 4 and 8 week evaluation time points.

Skin Rebound Time (Seconds)

| Subject No. | Baseline L | Baseline R | Week 4 L | Week 4 R | Week 8 L | Week 8 R |
|---|---|---|---|---|---|---|
| 1 | 2.14 | 3.51 | 1.84 | 2.04 | 1.25 | 1.51 |
| 2 | 3.94 | 2.55 | 1.74 | 1.96 | 1.58 | 1.20 |
| 3 | 2.34 | 2.31 | 1.31 | 1.36 | 0.66 | 0.86 |
| 4 | 3.36 | 2.97 | 1.83 | 2.20 | 1.39 | 1.18 |
| 5 | 2.25 | 2.62 | 1.30 | 1.49 | 1.11 | 1.53 |
| 6 | 2.14 | 2.24 | 1.94 | 1.75 | 1.02 | 1.17 |
| 7 | 2.36 | 2.48 | 2.34 | 2.32 | 1.45 | 2.62 |
| 8 | 2.84 | 2.13 | 1.93 | 1.58 | 2.01 | 1.44 |
| 9 | 1.98 | 1.32 | 1.01 | 0.98 | 1.02 | 0.98 |
| 10 | 3.44 | 1.70 | 2.14 | 2.18 | 1.20 | 1.80 |
| 11 | 2.95 | 2.20 | 1.36 | 1.36 | 1.36 | 1.08 |
| 12 | 1.55 | 2.06 | 1.40 | 1.65 | 0.90 | 0.88 |
| 13 | 1.50 | 2.02 | 1.33 | 1.53 | 1.24 | 0.98 |
| 14 | 1.64 | 1.58 | 1.30 | 1.58 | 0.92 | 0.95 |
| 15 | 1.14 | 1.20 | 0.77 | 0.83 | 0.56 | 0.58 |
| 16 | 2.17 | 2.10 | 1.48 | 1.38 | 0.95 | 1.39 |
| 18 | 2.02 | 2.25 | 2.27 | 2.14 | 2.25 | 1.74 |
| 19 | 2.02 | 2.65 | 2.14 | 2.02 | 1.31 | 1.40 |
| 20 | 1.14 | 1.18 | 1.21 | 1.17 | 1.20 | 0.82 |
| 21 | 2.08 | 1.20 | 1.10 | 1.14 | 0.86 | 0.82 |
| 22 | 2.02 | 1.29 | 1.58 | 1.27 | 1.14 | 1.04 |
| 23 | 1.02 | 1.28 | 1.72 | 1.63 | 1.04 | 0.89 |
| 24 | 2.61 | 2.65 | 2.67 | 1.74 | 1.02 | 1.53 |
| 25 | 2.29 | 2.13 | 1.92 | 1.48 | 1.04 | 1.20 |
| 26 | 1.68 | 1.00 | 0.98 | 1.05 | 0.48 | 0.73 |
| 27 | 1.44 | 1.29 | 1.19 | 1.20 | 1.02 | 0.90 |
| 28 | 1.74 | 2.20 | 1.48 | 1.23 | 1.49 | 1.20 |
| 29 | 1.59 | 2.02 | 1.59 | 1.65 | 1.35 | 1.68 |
| 30 | 1.04 | 1.21 | 0.99 | 0.73 | 0.87 | 0.57 |
| 31 | 2.21 | 1.37 | 2.20 | 1.17 | 1.92 | 0.80 |
| Means = | 2.09 | 1.96 | 1.60 | 1.53 | 1.19 | 1.18 |

Discontinued from study: Subject #17-data not included

Dependent t-test

| Baseline vs | Left Week 4 | Left Week 8 | Right Week 4 | Right Week 8 |
|---|---|---|---|---|
| t | 4.237 | 7.415 | 5.378 | 8.289 |
| df | 29 | 29 | 29 | 29 |
| Two-tailed p< | 0.000 | 0.000 | 0.000 | 0.000 |
| r | 0.492 | 0.384 | 0.721 | 0.590 |
|  | Sig. | Sig | Sig. | Sig. |

*FIG. 3*

| Subject Demographics ||||||
|---|---|---|---|---|---|
| Subject Number | Age | Sex | Subject Number | Age | Sex |
| 1 | 62 | F | 16 | 60 | M |
| 2 | 57 | F | 18 | 56 | F |
| 3 | 44 | F | 19 | 65 | F |
| 4 | 60 | F | 20 | 47 | F |
| 5 | 48 | M | 21 | 43 | F |
| 6 | 61 | F | 22 | 55 | F |
| 7 | 64 | F | 23 | 40 | F |
| 8 | 52 | M | 24 | 52 | F |
| 9 | 42 | F | 25 | 57 | M |
| 10 | 65 | F | 26 | 60 | F |
| 11 | 57 | F | 27 | 59 | M |
| 12 | 49 | M | 28 | 59 | M |
| 13 | 58 | F | 29 | 49 | M |
| 14 | 63 | M | 30 | 49 | F |
| 15 | 40 | F | 31 | 49 | F |

FIG. 4

Panelist Demographics

| Subject Number | Subject Initials | CRL ID # | Age | Sex |
|---|---|---|---|---|
| 1 | GC | 18705 | 68 | F |
| 2 | CG | 06152 | 49 | F |
| 3 | LH | 21025 | 58 | F |
| 4 | SH | 21327 | 42 | F |
| 5 | KR | 19875 | 63 | F |
| 6 | JG | 17785 | 56 | F |
| 7 | EM | 19485 | 56 | F |
| 8 | MZ | 07414 | 48 | F |
| 9 | BM | 00087 | 62 | F |
| 10 | BR | 00658 | 63 | F |
| 11 | DA | 21305 | 33 | F |
| 12 | ES | 20392 | 59 | F |
| 13 | ZM | 09802 | 65 | F |
| 14 | AP | 03256 | 41 | F |
| 15 | CS | 18615 | 50 | F |
| 16 | MD | 16469 | 59 | F |
| 17 | DB | 14756 | 37 | F |
| 18 | KL | 21422 | 52 | F |
| 19 | RL | 14720 | 44 | F |
| 20 | EC | 04349 | 58 | F |
| 21 | MB | 09559 | 64 | F |

FIG. 5

Measurement Randomization

| Subject Number | Measured Side of the Face |
|---|---|
| 1 | RIGHT |
| 2 | LEFT |
| 3 | RIGHT |
| 4 | RIGHT |
| 5 | LEFT |
| 6 | LEFT |
| 7 | LEFT |
| 8 | RIGHT |
| 9 | LEFT |
| 10 | RIGHT |
| 11 | LEFT |
| 12 | LEFT |
| 13 | LEFT |
| 14 | RIGHT |
| 15 | RIGHT |
| 16 | LEFT |
| 17 | RIGHT |
| 18 | RIGHT |
| 19 | RIGHT |
| 20 | LEFT |
| 21 | RIGHT |

FIG. 6
Treatment/Group Randomization

| Subject Number | Supplement Treatment/Group |
|---|---|
| 1 | A |
| 2 | A |
| 3 | A |
| 4 | B |
| 5 | A |
| 6 | B |
| 7 | B |
| 8 | A |
| 9 | B |
| 10 | A |
| 11 | B |
| 12 | B |
| 13 | A |
| 14 | B |
| 15 | A |
| 16 | B |
| 17 | B |
| 18 | B |
| 19 | A |
| 20 | A |
| 21 | B |

A=Group 1 Subjects assigned to the raw ingredient test material supplement, 10853LLA
B=Group 2 Subjects assigned to the placebo test material supplement, 10853LLB

FIG. 7A

Statistical Analysis of Cutometer Readings

| 10853LLA (raw ingredient test material supplement) Comparison of Cutometer Measurements - Parameter Ur/Ue Between Baseline, Week 8 and Week 12 | | | | |
|---|---|---|---|---|
| Tukey Grouping * | | Mean | N | Interval |
|  | A | 0.4723 | 10 | Week 12 |
| B | A | 0.4109 | 10 | Week 8 |
| B |  | 0.3752 | 10 | Baseline |
| * Means with the same letter are not significantly different | | | | |

| 10853LLA (raw ingredient test material supplement) Comparison of Cutometer Measurements - Parameter Uv/Ue Between Baseline, Week 8 and Week 12 | | | |
|---|---|---|---|
| Tukey Grouping * | Mean | N | Interval |
| A | 0.8626 | 10 | Week 12 |
| A | 0.7695 | 10 | Week 8 |
| A | 0.7000 | 10 | Baseline |
| * Means with the same letter are not significantly different | | | |

| 10853LLA (raw ingredient test material supplement) Comparison of Cutometer Measurements - Parameter Ur/Uf Between Baseline, Week 8 and Week 12 | | | |
|---|---|---|---|
| Tukey Grouping * | Mean | N | Interval |
| A | 0.2566 | 10 | Week 12 |
| A | 0.2345 | 10 | Week 8 |
| A | 0.2279 | 10 | Baseline |
| * Means with the same letter are not significantly different | | | |

FIG. 7B

Statistical Analysis of Cutometer Readings

| 10853LLB (placebo supplement) Comparison of Cutometer Measurements - Parameter Ur/Ue Between Baseline, Week 8 and Week 12 | | | | |
|---|---|---|---|---|
| Tukey Grouping * | | Mean | N | Interval |
|  | A | 0.5107 | 10 | Week 12 |
| B | A | 0.4530 | 10 | Baseline |
| B |  | 0.3800 | 10 | Week 8 |
| * Means with the same letter are not significantly different | | | | |

| 10853LLB (placebo supplement) Comparison of Cutometer Measurements - Parameter Uv/Ue Between Baseline, Week 8 and Week 12 | | | |
|---|---|---|---|
| Tukey Grouping * | Mean | N | Interval |
| A | 0.8171 | 10 | Week 12 |
| A | 0.7876 | 10 | Baseline |
| A | 0.6629 | 10 | Week 8 |
| * Means with the same letter are not significantly different | | | |

| 10853LLB (placebo supplement) Comparison of Cutometer Measurements - Parameter Ur/Uf Between Baseline, Week 8 and Week 12 | | | | |
|---|---|---|---|---|
| Tukey Grouping * | | Mean | N | Interval |
|  | A | 0.2839 | 10 | Week 12 |
| B | A | 0.2554 | 10 | Baseline |
| B | A | 0.2313 | 10 | Week 8 |
| * Means with the same letter are not significantly different | | | | |

FIG. 7C

Statistical Analysis of Cutometer Readings

| Cutometer Measurements Percentage Changes from Baseline between: 10853LLA (raw ingredient test material supplement) and 10853LLB (placebo supplement) at Week 8 and Week 12 ||||
|---|---|---|---|
| Comparison | Parameter | Time Interval | P-value |
| 10853LLA versus 10853LLB | Ur/Ue | Week 8 | 0.1454 |
| | | Week 12 | 0.5623 |
| | Uv/Ue | Week 8 | 0.2183 |
| | | Week 12 | 0.4568 |
| | Ur/Uf | Week 8 | 0.2427 |
| | | Week 12 | 0.7457 |

FIG. 7D

Statistical Analysis of Cutometer Readings

| Cutometer Measurements Parameter Ur/Ue 10853LLA (raw ingredient test material supplement) at Week 8 and Week 12 ||||
|---|---|---|---|
| Comparison | Parameter | Time Interval | P-value |
| Baseline versus Post-Application | Ur/Ue | Week 8 | 0.3161 |
| | | Week 12 | 0.0109* |

\* Statistically Significant - Statistical significance was declared for all p-values less than or equal to 0.05, at a 95% confidence level.

FIG. 8A

Questionnaire Responses - Week 12 (Final) Questionnaire
For Group 1 Subjects (assigned to the raw ingredient test material supplement, 10853LLA)
After using the product for 12 weeks, I experience muscle and/or joint pain less frequently:

|  | Responses | | | | | Z-Score | Significant |
|---|---|---|---|---|---|---|---|
|  | Strongly agree | Somewhat agree | Neither agree nor Disagree | Somewhat disagree | Strongly disagree | | |
| Number of Subjects | 3 | 5 | 1 | 1 | 0 | 2.21 | Yes |
| Proportion of Subjects | 30.0% | 50.0% | 10.0% | 10.0% | 0.0% | | |
| Split Proportions | 85.0% | | | 15.0% | | | |

After using the product for 12 weeks, the overall pain has been less intense:

|  | Responses | | | | | Z-Score | Significant |
|---|---|---|---|---|---|---|---|
|  | Strongly agree | Somewhat agree | Neither agree nor Disagree | Somewhat disagree | Strongly disagree | | |
| Number of Subjects | 4 | 4 | 1 | 1 | 0 | 2.21 | Yes |
| Proportion of Subjects | 40.0% | 40.0% | 10.0% | 10.0% | 0.0% | | |
| Split Proportions | 85.0% | | | 15.0% | | | |

After using the product for 12 weeks, the pain did not last as long:

|  | Responses | | | | | Z-Score | Significant |
|---|---|---|---|---|---|---|---|
|  | Strongly agree | Somewhat agree | Neither agree nor Disagree | Somewhat disagree | Strongly disagree | | |
| Number of Subjects | 3 | 6 | 0 | 1 | 0 | 2.53 | Yes |
| Proportion of Subjects | 30.0% | 60.0% | 0.0% | 10.0% | 0.0% | | |
| Split Proportions | 90.0% | | | 10.0% | | | |

FIG. 8B

Questionnaire Responses - Week 12 (Final) Questionnaire
For Group 1 Subjects (assigned to the raw ingredient test material supplement, 10853LLA)

The product had a positive effect on my joint and/or muscle pain:

|  | Responses ||||| Z-Score | Significant |
| --- | --- | --- | --- | --- | --- | --- | --- |
|  | Strongly agree | Somewhat agree | Neither agree nor Disagree | Somewhat disagree | Strongly disagree |  |  |
| Number of Subjects | 2 | 6 | 1 | 1 | 0 | 2.21 | Yes |
| Proportion of Subjects | 20.0% | 60.0% | 10.0% | 10.0% | 0.0% |  |  |
| Split Proportions | 85.0% ||| 15.0% || | |

Over the last week, I did not feel a need for any oral or topical pain medication:

|  | Responses ||||| Z-Score | Significant |
| --- | --- | --- | --- | --- | --- | --- | --- |
|  | Strongly agree | Somewhat agree | Neither agree nor Disagree | Somewhat disagree | Strongly disagree |  |  |
| Number of Subjects | 3 | 2 | 2 | 2 | 1 | 0.63 | No |
| Proportion of Subjects | 30.0% | 20.0% | 20.0% | 20.0% | 10.0% |  |  |
| Split Proportions | 60.0% ||| 40.0% || | |

I would purchase this product to help with joint and/or muscle pain:

|  | Responses ||||| Z-Score | Significant |
| --- | --- | --- | --- | --- | --- | --- | --- |
|  | Strongly agree | Somewhat agree | Neither agree nor Disagree | Somewhat disagree | Strongly disagree |  |  |
| Number of Subjects | 4 | 2 | 1 | 2 | 1 | 0.95 | No |
| Proportion of Subjects | 40.0% | 20.0% | 10.0% | 20.0% | 10.0% |  |  |
| Split Proportions | 65.0% ||| 35.0% || | |

FIG. 9A

Questionnaire Responses - Week 12 (Final) Questionnaire
For Group 2 Subjects (assigned to the placebo supplement, 10853LLB)

After using the product for 12 weeks, I experience muscle and/or joint pain less frequently:

|  | Responses ||||| Z-Score | Significant |
|---|---|---|---|---|---|---|---|
|  | Strongly agree | Somewhat agree | Neither agree nor Disagree | Somewhat disagree | Strongly disagree |  |  |
| Number of Subjects | 1 | 1 | 2 | 3 | 3 | -1.26 | No |
| Proportion of Subjects | 10.0% | 10.0% | 20.0% | 30.0% | 30.0% |  |  |
| Split Proportions | 30.0% ||| 70.0% |||||

After using the product for 12 weeks, the overall pain has been less intense:

|  | Responses ||||| Z-Score | Significant |
|---|---|---|---|---|---|---|---|
|  | Strongly agree | Somewhat agree | Neither agree nor Disagree | Somewhat disagree | Strongly disagree |  |  |
| Number of Subjects | 1 | 2 | 1 | 3 | 3 | -0.95 | No |
| Proportion of Subjects | 10.0% | 20.0% | 10.0% | 30.0% | 30.0% |  |  |
| Split Proportions | 35.0% ||| 65.0% |||||

After using the product for 12 weeks, the pain did not last as long:

|  | Responses ||||| Z-Score | Significant |
|---|---|---|---|---|---|---|---|
|  | Strongly agree | Somewhat agree | Neither agree nor Disagree | Somewhat disagree | Strongly disagree |  |  |
| Number of Subjects | 1 | 3 | 1 | 3 | 2 | -0.32 | No |
| Proportion of Subjects | 10.0% | 30.0% | 10.0% | 30.0% | 20.0% |  |  |
| Split Proportions | 45.0% ||| 55.0% |||||

FIG. 9B

Questionnaire Responses - Week 12 (Final) Questionnaire
For Group 2 Subjects (assigned to the placebo supplement, 10853LLB)

The product had a positive effect on my joint and/or muscle pain:

|  | Responses ||||| Z-Score | Significant |
|---|---|---|---|---|---|---|---|
|  | Strongly agree | Somewhat agree | Neither agree nor Disagree | Somewhat disagree | Strongly disagree |  |  |
| Number of Subjects | 1 | 3 | 1 | 3 | 2 | -0.32 | No |
| Proportion of Subjects | 10.0% | 30.0% | 10.0% | 30.0% | 20.0% |  |  |
| Split Proportions | 45.0% ||| 55.0% |||||

Over the last week, I did not feel a need for any oral or topical pain medication:

|  | Responses ||||| Z-Score | Significant |
|---|---|---|---|---|---|---|---|
|  | Strongly agree | Somewhat agree | Neither agree nor Disagree | Somewhat disagree | Strongly disagree |  |  |
| Number of Subjects | 1 | 3 | 2 | 1 | 3 | 0.00 | No |
| Proportion of Subjects | 10.0% | 30.0% | 20.0% | 10.0% | 30.0% |  |  |
| Split Proportions | 50.0% ||| 50.0% |||||

I would purchase this product to help with joint and/or muscle pain:

|  | Responses ||||| Z-Score | Significant |
|---|---|---|---|---|---|---|---|
|  | Strongly agree | Somewhat agree | Neither agree nor Disagree | Somewhat disagree | Strongly disagree |  |  |
| Number of Subjects | 1 | 2 | 1 | 3 | 3 | -0.95 | No |
| Proportion of Subjects | 10.0% | 20.0% | 10.0% | 30.0% | 30.0% |  |  |
| Split Proportions | 35.0% ||| 65.0% |||||

ALOE PREPARATION FOR SKIN ENHANCEMENT

CROSS-REFERENCE TO RELATED APPLICATIONS

This application claims the benefit of the filing date of U.S. Provisional Patent Application No. 60/928,924, filed May 11, 2007, the disclosure of which is hereby incorporated herein by reference.

BACKGROUND OF THE INVENTION

In one aspect, the present invention relates to the use of bioactive compositions produced, isolated, extracted, based on or derived from either an *Aloe vera* plant or a portion thereof, for skin enhancement and for pain relief. The invention also relates to immunostimulatory compositions, stabilized immunostimulatory compositions, and methods of making and using such compositions.

The genus *Aloe* (Liliaceae) is a shrubby tropical/subtropical plant which has succulent and elongated leaves. Of the more than 360 *Aloe* species known, *Aloe barbadensis* Miller (*Aloe vera* Linne) is the most widely used, both commercially and for its therapeutic properties. *Aloe vera* plants contain two major juice materials: first, a yellow exudate containing a high concentration of anthraquinone compounds that has been used throughout the centuries as a cathartic and for medicinal purges; and second, a clear mucilaginous gel that has been used since ancient times to treat burns and other wounds where it is thought to increase the rate of healing and reduce the risk of infection. See Grindlay, D. Reynolds, T., J. Ethnopharmcol. 1986, 16(2-3), 117-151; and Joshi, S. P., J. Med. Aromat. Plant Sci. 1998, 20(3), 768-773.

For centuries, the *Aloe* plant has been considered to have, and has been used, for its medicinal and therapeutic properties without any clear understanding or scientific analysis of the bases for such properties. Aristotle was aware that the healing properties of *Aloe* would be invaluable to soldiers wounded in battle and advised his student Alexander III ("the Great") to conquer all lands that grew it, especially the island of Socotra off the coast of eastern Africa. Pedanius Dioscorides, a physician in the Roman army, mentioned medicinal *Aloe*s in his encyclopedic Greek herbal De Materia Medica (approximately 75 BC). Further, it is known that the biological activities of fresh *Aloe* plant decay quite rapidly.

Over that past few decades there has been a high level of interest in developing an understanding of the active components of *Aloe* that are responsible for its beneficial effects relating to enhanced immune function. The research in this area has focused largely on polysaccharides and other carbohydrate-containing substances such as glycoproteins.

Active chemical substances and mixtures, including for example, polysaccharides or other carbohydrate-containing substances of *Aloe* leaves have been identified, isolated and stabilized as described in U.S. Pat. Nos. 7,196,072, ("the '072 patent"), 5,902,796, 4,735,935, 4,851,224, 4,917,890, 4,957,907, 4,959,214, and 4,966,892.

One group of the active chemical substances has been referred to as *Aloe vera* mucilaginous polysaccharides, which are made up of a mixture of polysaccharides. The term "polysaccharides" has been used loosely to include both oligomers and polymers of carbohydrates or simple sugars and is used in a similar manner herein. One group of such polysaccharides has been given the name acemannan.

According to literature, acemannan is an ordered linear polymer of substantially acetylated mannose monomers available from Carrington Laboratories, Inc. (Irving, Tex.), and has been shown in laboratory studies to increase up to 300%, in 48 hours, the replication of fibroblasts in tissue culture, which are known to be responsible for healing burns, ulcers and other wounds of the skin and of the gastrointestinal lining.

Over a three year period, laboratory rats, the stomachs of which react similarly to that of humans, were tested. Acemannan was found to be equivalent to or superior to then current medications used for the treatment of gastric ulcers. Most such products acted to inhibit hydrochloric acid in the stomach. Acemannan worked on a different principle and apparently did not alter the natural flow of digestive acids. See U.S. Pat. No. 5,902,796, column 2, lines 20-25.

Acemannan has been shown to be an inducer of IL-I and prostaglandin E2 (PGE2) production by human peripheral blood adherent cells in culture. IL-I is an important macrophage product reported in the literature to influence the activity and production of lymphocytes, fibroblasts, B-lymphocytes and endothelial cells. See Old, *Scientific American*, 258(5):59-60, 69-75 (1988).

IL-1 induces fibroblast proliferation which is fundamental to wound healing. IL-1 also: (1) enhances bone marrow activity; it may be therapeutic in individuals whose bone-marrow is depressed; and (2) enhances the immune system in general.

According to literature, a series of experiments with mixed lymphocyte cultures (MLC) has shown that acemannan increases the alloantigenic response of these lymphocytes in a dose-related fashion. Incubation of acemannan with monocytes permitted monocyte-driven signals to enhance the T lymphocyte response to leetin. Related studies on acemannan's effects on MLC have shown an increase in phagocytosis and activity of natural killer cells. In these in vitro test systems, acemannan was allegedly non-toxic and an immunoenhancer.

Acemannan allegedly stimulates lymphocytes to secrete lymphokines and also causes HIV-infected lymphocytes to produce altered glycoproteins (GP-120) by a mechanism similar to that of glucosidase I inhibitors. See Gruters et al., Nature 330:74-77 (1987) and Pal et al., Intervirol. 30:27-35 (1989). Acemannan is phagocytized and apparently pumped to the Golgi/glycoprotein apparatus of the monocyte where it interferes directly with glycoprotein synthesis.

Other uses of *Aloe* products have been described in, for example, U.S. Pat. Nos. 5,106,616, 5,118,673, 5,308,838, 5,441,943, and 5,443,830. The described studies have primarily focused on the activities of bioactive chemical substances of *Aloe vera* as antiviral agents, antitumor agents, immunostimulants, immunomodulators, vaccine adjuvants, means of reducing opportunistic infections, means of controlling inflammation, means of stimulating the immune system and wound healing processes.

A number of other products based on polysaccharide-containing fractions isolated from *Aloe vera* have been published in the patent literature and elsewhere. For example, a polyuronide with a molecular weight between 275,000 and 374,000 daltons is reported to be useful in treatment of surface wounds. (See Farkas, A., U.S. Pat. No. 3,103,466 (1963).)

The 70 kD polysaccharide, Aloeferon, has also been reported to have therapeutic potential. (See Madis, V. H.; Omar, M. M.; Madis, V., U.S. Pat. No. 4,861,761 (1989).)

Other active components isolated from *Aloe* include a polysaccharide between 420,000 and 520,000 daltons comprised of equal amounts of glucose and mannose. (See Farkas, A., U.S. Pat. No. 3,362,951 (1968).)

In addition, several groups have enzymatically prepared altered polysaccharide compositions from the naturally occurring carbohydrates in *Aloe* (See Strickland, F. M.; Pelley, R. P.; Kripke, M. L., U.S. Pat. No. 5,824,659 (1998)).

*Aloe vera* polysaccharides have also been shown in controlled studies to increase the rate of healing in animals. *Aloe vera* polysaccharides have also been shown to be an effective treatment for gastric ulcers in animal studies.

Anti-inflammatory activity of *Aloe vera* gel has been reported by both oral testimonies and respected scientific journals. Rubel [Cosmetics and Toiletries, 98:109-114 (1983)] discussed the possible mechanism of the anti-inflammatory effect of *Aloe* gel. Ukai et al., [Journal of Pharmacobio-Dynamics, 6(12):983-990 (1983)] noted anti-inflammatory activity of polysaccharides extracted from the fruiting bodies of several fungi. The polysaccharides allegedly demonstrated a significant inhibitory effect on carrageenan-induced edema. One of the polymers, O-acetylated-D-mannan (T-2-HN), in addition demonstrated a more marked inhibitory effect than phenylbutazone on scald hyperalgesia. Ukai et al., supra. The assertion in this article, that the polysaccharide is allegedly free from protein and lipids suggests that the anti-inflammatory effect is due to the acetylated mannan only.

Other researchers have also reported anti-inflammatory effects of complex polysaccharides [Saeki et al., Japanese Journal of Pharmacology, 24(1):109-118 (1974)], glycoproteins [Arita et al., Journal of Biochemistry, 76(4):861-869 (1974)] and sulfated polysaccharides [Rocha et al., Biochemical Pharmacology, 18:1285-1295 (1969)].

It is therefore possible that mucilaginous gel, a component of the *Aloe vera* plant, which is essentially a polysaccharide, and components therein, are responsible in part for *Aloe vera*'s medicinal properties. The controversy over whether the polysaccharide is a glucomannan, mannan, pectin, or of some other composition, is allegedly resolved by a series of chemical purification steps. Yagi et al., [Planta Medica, 31(1):17-20 (1977)], using a slightly modified extraction method; isolated acetylated mannan (*Aloe mannan*) from *Aloe arborescens* Miller var. *natalensis*. Ovodova [Khim, Prior, Soedin, 11(1):325-331 (1975)], however, earlier isolated pectin as the main component of the same *Aloe* species.

A number of other pharmacology studies have been conducted on *Aloe vera* gel in recent times. Results have included more rapid healing of radiation burns [Rowe, J. Am. Pharm. Assoc., 29:348-350 (1940)] and accelerated healing of wounds [Lushbaugh et al., Cancer, 6:690-698 (1953)]. Thermal burns treated with *Aloe vera* gel heal much faster than untreated burns [Ashley et al., Plast. Reconstr. Surg., 20:383-396 (1957), Rovatto, supra, Rodriguez-Bigas et al., J. Plast. Reconstr. Surg., 81:386-389 (1988)]. The gel is useful in treating leg ulcers [El Zawahry et al., Int. J. Dermatol., 12:68-73 (1973)] and in hastening post surgical healing (Payne, Thesis submitted to Faculty of Baylor University, Waco, Tex., MS Degree). Experimental evidence suggests that extracts of *Aloe vera* have anti-infectious properties [Solar, Arch. Inst. Pasteur Madagascar, 47:9-39 (1979)] and enhance phagocytosis [Stepanova, Fiziol. Akt. Veshchestva, 9:94-97 (1977)].

During commercial processing and quality control of *Aloe* products, microbiological analysis is recognized as an important issue (Waller T A, et al. In *Aloes: The genus Aloe*; Reynolds T, Ed.; CRC Press: NY, 2004; Chapter 8, pp 139-205). Microbiological organisms can originate from both exogenous sources such as the environment and from within the *Aloe* plant itself. The endogenous bacterial flora are microorganisms that naturally exist within *Aloe* that have evolved to grow well in that unique environment. The primary interest in endogenous bacteria has been with respect to controlling its potential overgrowth that can result with improper post-harvest processing methods (e.g. lack of or incorrect pasteurization). Furthermore, it has been highlighted that high bacterial load in *Aloe* products is likely to result in loss of biological activity. This has been reported by the observation that high bacterial content (>100,000 organisms/gram of gel) is correlated with loss of Aloe's ability to protect the skin immune system from UVB-induced suppression (Waller T A, et al. In *Aloes: The genus Aloe*; Reynolds T, Ed.; CRC Press: NY, 2004; Chapter 8, pp 139-205).

References in the art describe bacterial components in *Aloe* with respect to endotoxin (also referred to as lipopolysaccharides) contamination as a confounding factor in evaluating the biological activity of purported active substances such acemannan polysaccharide. For example, this point was stressed by Tizard (Tizard I R and Ramamoorthy L. In *Aloes: The genus Aloe*; Reynolds T, Ed.; CRC Press: NY, 2004; Chapter 13, pp 311-332): "It is difficult to produce *Aloe* carbohydrate solutions free of contaminating endotoxin. Early studies on this material contained small but significant quantities of bacterial endotoxin and it is possible that some of the biological activities ascribed to acemannan may have been endotoxin effects". Thus, bacterial products in *Aloe* preparations are considered contaminants.

U.S. Pat. No. 5,902,796 describes various methods and separation processes for obtaining different factors from *Aloe vera*. One factor described is called a "microparticulate factor" that can be obtained as a pellet by centrifugation at 20,000 g of the supernatant obtained from a low speed centrifugation (180 g) of an *Aloe* solution. Methods are also described for obtaining this factor using filtration. This microparticulate factor is an activator of macrophages. The size of this microparticulate factor is estimated to be approximately 1 µm.

The characterization of the microparticles was described in a later paper (Ni Y, et al, *International Immunopharmacology*, 2004, 4: 1745-1755). The microparticles were reported to contain galactose-rich polysaccharide(s) with the following composition: 40.2% galactose, 32.2% mannose, 20.6% glucose and other minor sugars. This paper identifies the microparticles as degenerated cellular organelles of mesophyll cells, as summarized: "Following disruption of pulp by homogenization, three components were isolated by sequential centrifugation. They were thin clear sheets, microparticles and a viscous liquid gel, which correspond to cell wall, degenerated cellular organelles and liquid content of mesophyll cells based on morphological and chemical analysis". Clearly these microparticles are not believed to be bacteria but rather have a defined carbohydrate composition and are plant structural components (i.e. degenerated cellular organelles of mesophyll cells).

Gram positive *micrococcus* bacterial species are the most prevalent *Aloe*-associated organisms. These bacteria have evolved to grow well within the *Aloe* plant and do not grow very well in other environments (Waller T A, et al. In *Aloes: The genus Aloe*; Reynolds T, Ed.; CRC Press: NY, 2004; Chapter 8, pp 139-205).

Recent research indicates that consumption of foods containing certain gram positive bacteria can have a beneficial effect on the immune system. This has been most extensively studied with respect to the ingestion of the probiotic lactic acid bacteria *Lactobacillus* and *Bifidobacterium* strains found in yoghurt and similar foods (See, *Nutr Rev.*, 2006, 64: 1-14). Many of these immune enhancing effects do not require viable bacterial cells since they can be mimicked by consumption of heat killed organisms.

Problems often associated with aging include a loss of skin elasticity and muscle or joint pain. These symptoms may or may not be related and while significant steps are being made in the understanding of the aging process, much is still unknown. Treatments for skin elasticity are often cosmetic in nature only. By covering the skin with a cosmetic, a more youthful appearance can be obtained in some instances. Some products actually glue the loose skin making it appear more taught. There are also surgical methods which can involve removing excess skin and/or tightening the skin in procedures commonly referred to as "face lifts". If, however, skin elasticity could be improved by the use of preparations which are ingested or applied topically, and which actually effect the elasticity of the skin directly, surgery could be postponed or avoided completely and fewer cosmetic products might be needed.

Similarly, there are many possible causes of joint pain including arthritis and many strategies to treat them. These include topical products, pharmaceutical preparations and even joint replacement surgery. Still, as to either joint pain, or skin elasticity, improvements in cure methods are necessary. If a product whose active ingredient is all-natural could be used to provide primary relief, or could be combined with other strategies, the results would be highly desirable.

SUMMARY OF THE INVENTION

The present invention relates to, in one aspect, *Aloe vera* derived materials exhibiting at least a certain amount of immunostimulatory activity ("IAvDs"). The degree of immunostimulatory activity required to qualify as an IAvD as measured by NF-kappa Beta directed luciferase expression in THP-1 monocytes at a concentration of about 250 µg/mL or less is at least about 50% of the maximal NF-kappa Beta directed luciferase expression achieved by bacterial lipo-polysaccharide at a concentration of about 10 µg/mL. The standard for this measurement is crude bacterial lipo-polysaccharide "ELPS" (*E. coli*, serotype 026:B6) obtained from Sigma Chemical Co.).

Another aspect of the invention is compositions comprising a mixture of lipo-proteins, and lipo-polysaccharides, and optionally, also at least one polysaccharide, all of which can be isolated from *Aloe vera*, although the mixture can be produced synthetically. The mixtures are referred to herein as "PLL". IAvD and PLL mixtures may contain two or more materials, in any combination. These mixtures may be blended with pharmaceutical carriers or excipients.

In a preferred embodiment, an immunostimulatory composition comprises a mixture of at least any two of (1) aloe-derived polysaccharides, (2) aloe-derived lipo-proteins, and (3) aloe-derived lipo-polysaccharides, the mixture exhibiting an immunostimulatory activity of at least about 50% of a maximal NF-kappa Beta directed luciferase expression achieved by a bacterial lipo-polysaccharide at a concentration of about 10 µg/mL, wherein the immunostimulatory activity is measured by NF-kappa Beta directed luciferase expression in THP-1 monocytes at a concentration of about 250 µg/mL or less.

The mixture may comprise aloe-derived polysaccharides, aloe-derived lipo-proteins, and aloe-derived lipo-polysaccharides In a preferred embodiment, the PLL is a particular mixture, referred to herein as "AloeEx", comprising 1) the *Aloe vera* derived polysaccharide disclosed in the '072 patent, the disclosure of which is hereby incorporated by reference, 2) *Aloe*-derived lipo-proteins "ALP", and 3) *Aloe*-derived lipo-polysaccharides "ALPS". Preferably, this mixture includes sufficient immunostimulatory activity to qualify as an IAvD as described herein.

Preferably, the PLL comprises between about 0.01% and about 50% by weight of the Aloeride polysaccharide and between about 0.0001% and about 10% ALPs and ALPSs (the total combined amount of ALPs and ALPSs) by weight. In other embodiments, the Aloeride polysaccharide comprises between about 1% and about 15% by weight and between about 0.0001% and about 10% ALPs and ALPSs by weight. In another embodiment, the Aloeride polysaccharide is about 10-15% by weight and the ALPs and ALPSs are between about 0.0001% to about 10% by weight of the IAvD.

It is believed that these ALPS and ALPSs are actually from microorganisms associated with *Aloe vera*. It is also believed that ALPs and ALPSs possess independent immunostimulatory properties. These may be used in addition to, or instead of immunostimulatory *Aloe*-derive polysaccharides, including for example, those of the '072 patent, to provide various benefits in the treatment or prevention of, among other things, any condition previously described in the art in conjunction with prior *Aloe* derivatives, such as treatment of burns and wounds, treatment of ulcers of the skin and of the gastrointestinal tract, enhancing bone marrow activity in individuals whose bone marrow is depressed, enhancing the immune system in general, as an antiviral agent, antitumor agent, immunostimulant, immunomodulator, vaccine adjuvant, means for reducing infections, means of controlling inflammation, means of stimulating the wound healing process, means for increasing the rate of healing, inhibiting scald hyperalgesia, rapid healing of radiation burns and thermal burns, treating leg ulcers, hastening post surgical healing, anti-infectious applications, enhancing phagocytosis, treatment of immunodeficiency disorders, cancer, infectious diseases or other diseases and conditions, amelioration of symptoms, decreasing muscle and joint pain, improving metabolic processes, improving the appearance, texture, firmness and/or elasticity of skin, and as a dietary supplement or nutritional aid.

In another aspect of the invention, immunostimulatory composition comprises aloe-derived lipo-proteins. The aloe-derived lipo-proteins exhibit an immunostimulatory activity of at least about 50% of a maximal NF-kappa Beta directed luciferase expression achieved by a bacterial lipo-polysaccharide at a concentration of about 10 µg/mL, wherein the immunostimulatory activity is measured by NF-kappa Beta directed luciferase expression in THP-1 monocytes at a concentration of about 250 µg/mL or less.

In another aspect of the invention, the composition is a pharmaceutical composition comprising one or more IAvD. In one embodiment, the composition is a pharmaceutical composition comprising one or more PLL in combination with pharmaceutical carriers or excipients. In a preferred embodiment, the PLL is AloeEx. These pharmaceutical compositions may be used for any of the purposes described immediately above in connection with PLLs.

Certain IAvDs that are useful in accordance with the present invention may be difficult to work with and formulate. There may be problems dispersing or dissolving particular IAvDs and producing homogenous mixtures thereof. This can be particularly problematic when formulating dosage forms. Nonhomogenous mixtures risk an unacceptable level of dose variation from dosage form to dosage form and therefore dose to dose. Finding suitable processing aides, solvents or excipients that are compatible with IAvDs and do not negatively affect the immunostimulatory properties or stability of the IAvDs and even more preferably do not unnecessarily dilute the activity thereby requiring larger quantities of more expensive materials, would therefore be highly desirable.

In accordance with another aspect of the invention, various "second" materials can be used in connection with a PLL or IAvD. It has been discovered that combinations with "second" materials can allow for the production of a homogenous dispersion, emulsion, suspension or solution and the like of a PLL or IAvD. These "second" materials may or may not be *Aloe*-derived materials and indeed may or may not be IAvDs (for example, they may not be sufficiently immunostimulatory to qualify as an IAvD as defined herein).

In one preferred embodiment, however, these second materials are derived from *Aloe vera*. In particular, it has been found that certain highly active first IAvDs can be dispersed, suspended, emulsified and/or solubilized by using a second *Aloe*-derived material, which, in some preferred embodiments are second IAvDs, e.g., *Aloe*-derived materials that meet the activity requirements set forth herein for IAvDs.

In other preferred embodiments the second materials are *Aloe*-derived materials which, if they have any immunostimulating activity at all, exhibit activity at a level below that of an IAvD. These second, non-IAvD *Aloe*-derived materials generally have a significant polysaccharide content wherein about 50% or more of the polysaccharides are of a molecular weight of about 1,500,000 daltons or less. For example, MagnAloe AG at 250 μg/ml exhibits less than 25% activation.

Moreover, these second materials should also improve or enhance the processability of the first IAvD. The amount of this second *Aloe*-derived material used (whether a second IAvD or a second non-IAvD) should be an amount which is sufficient to allow for the production of, as desired, a homogenous dispersion, solution, suspension, or emulsion of a first IAvD. Generally at least about 10% of this second *Aloe*-derived material is required, by weight percent, relative to the weight percent of the first IAvD and the second *Aloe*-derived material.

In a preferred embodiment in accordance with the present invention, the first material is a PLL and the second material is an *Aloe*-derived material which is not an IAvD, has a polysaccharide content as discussed above (generally at least 50% less than 1,500,000 daltons) and permits the formation of a stable, homogeneous dispersion, solution, suspension, or emulsion. In a particularly preferred embodiment, the PLL is AloeEx and the second material is MagnAloe AG. Methods of making these formulations are also contemplated.

In still another aspect of the invention, there is provided a method of treating muscle or joint pain, for improving the appearance, texture, firmness and/or elasticity of skin and/or for providing accelerated growth of new skin cells comprising administering, to an individual in need thereof, a therapeutic dose of an IAvD or PLL composition. The composition may be administered orally, topically or transdermally, once or several times a day and may be administered alone, with a pharmaceutically acceptable carrier or excipient, and/or with other active or inactive ingredients.

In one embodiment of this aspect, the IAvD is a PLL.
In a particular embodiment, the PLL is AloeEx.

In another embodiment, the IAvD composition comprises an *Aloe* derived polysaccharide or mixture of polysaccharides, such as, without limitation, an *Aloe*-derived polysaccharide such as that described in the '072 patent.

Another aspect of the invention is a method for preparing an IAvD comprising providing an *Aloe vera* source material; extracting a liquid *Aloe* solution from the *Aloe vera* source material; filtering the liquid *Aloe* solution; adding a flocculent, thereby creating aggregates containing microorganisms or microorganism components/fragments; and collecting the aggregates.

In another embodiment, the collected aggregates can be processed to remove anthraquinones, if present.

In an embodiment, the *Aloe vera* source material is selected from the group consisting of *Aloe vera* gel, whole leaf *Aloe vera*, *Aloe vera* rind, *Aloe vera* mucilage and *Aloe vera* pups. *Aloe vera* pups are small *Aloe vera* plants usually considered a waste product.

In a preferred embodiment, the *Aloe vera* source material comprises *Aloe vera* rind and *Aloe vera* mucilage. Other *Aloe* based materials, such as spent *Aloe* materials typically considered as waste materials from other processes may be used.

In another aspect of the invention, method for preparing a chemically standardized *Aloe vera* derived material comprises: providing an *Aloe vera* derived material; determining the content of 2,3-dihydroxypropyl cysteine in the *Aloe vera* derived material; and comparing the amount of 2,3-dihydroxypropyl cysteine in the *Aloe vera* derived material to the amount of 2,3-dihydroxypropyl cysteine in a standard preparation, thereby determining a standardized value for the *Aloe vera* derived material.

In one embodiment, the method further comprises purifying the *Aloe vera* derived material prior to determining the content of 2,3-dihydroxypropyl cysteine in the *Aloe vera* derived material.

In yet another aspect of the invention a method for preparing a biologically standardized *Aloe vera* derived material comprises: providing an *Aloe vera* derived material; determining the level of activation of immune cells of the *Aloe vera* derived material; and comparing the level of activity of the *Aloe vera* derived material to a standard immunostimulatory value, thereby determining a standardized activity value of the *Aloe vera* derived material.

In one embodiment, the method further comprises purifying the *Aloe vera* derived material prior to determining the level of activation of immune cells of the *Aloe vera* derived material.

In another aspect of the invention a method of enhancing immune function comprises administering, to an individual in need thereof, a therapeutic dose of at least one IAvD.

BRIEF DESCRIPTION OF THE DRAWINGS

FIG. 1 depicts the glcosyl residue composition of AloeEx Batch 56 (ALOE 056) by mole % of total carbohydrate.

FIG. 2 depicts a statistically significant decrease in mean skin rebound time in seconds (an indicator of an increase in skin elasticity or firmness).

FIG. 3 identifies skin elasticity study demographics by gender and age.

FIG. 4 depicts study panelist demographics.

FIG. 5 identifies measurement randomization parameters.

FIG. 6 identifies treatment/group randomization.

FIGS. 7A-7D depict the statistical analysis of Cutometer measurements for both the test material group and the placebo group.

FIGS. 8A-8B depict questionnaire results for test subjects assigned the active treatment.

FIGS. 9A-9B depict questionnaire results for test subjects assigned the placebo treatment.

DETAILED DESCRIPTION

Figure 10A:
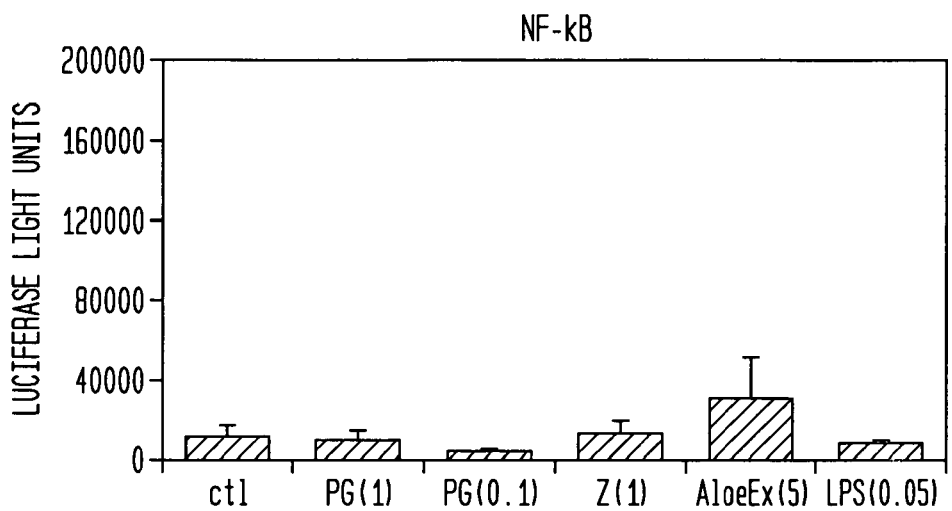
FIGS. 10A-10B depict that TLR2 is involved in NF-kappa B activation by AloeEx.

While the specification concludes with the claims particularly pointing and distinctly claiming the invention, it is believed that the present invention will be better understood from the following description.

All percentages and ratios used herein are by weight of the total composition and all measurements made are at 25° C. and normal pressure unless otherwise designated.

All temperatures are in Degrees Celsius unless specified otherwise.

The present invention can comprise (open ended) or consist essentially of the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention. Preferably, such additives will not be present at all or only in trace amounts. However, it may be possible to include up to about 10% by weight of materials that could materially alter the basic and novel characteristics of the invention as long as the utility of the compositions (as opposed to the degree of utility) is maintained.

All ranges recited herein include the endpoints, including those that recite a range "between" two values. Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

Note that while the specification and claims may refer to a tablet or other dosage form of the invention as, for example, containing particles having a certain particle size or distribution, or a certain type of, for example, a filler, it may be difficult to tell from the final dosage form that the recitation is satisfied. However, such a recitation may be satisfied if the materials used prior to final blending and formulation, for example, meet that recitation.

In another example, while it might be difficult to know the weight gain that the coating contributed to a coated particle or its particle size distribution as it actually exists in a finished dosage form, if it is determined that the coated particles used to make the dosage form, prior to, in the case of a tablet, for example, a final blending and compression step, did exhibit the desired coating level and/or particle size, that is sufficient.

Indeed here, it might be difficult to establish the content of a particular component in a particular formulation or the activity of a particular component in the final formulation. If this can be established based on the starting or intermediate materials, it is sufficient. Indeed, as to any property which cannot be ascertained from the finished product directly, it is sufficient if that property resides in the formulation just prior to final production. It will be appreciated that immunostimulatory activity sufficient to define an IAvD as described herein may be established any time before or after formulation.

As used herein, treatment and/or improvement, when used in connection with joint pain or skin elasticity, or indeed other conditions described herein, refers to any lessening, whether permanent or temporary, lasting or transient, of joint or muscle pain or any increase in skin elasticity that can be attributed to or associated with administration of the PLL and/or IAvD composition. Treatment and improvement also include use of products as described herein to prevent a condition or its recurrence. Note also that improvement and treatment are used interchangeably, unless the text or context dictate otherwise.

In particular, to qualify as an IAvD herein, a material must substantially contribute to the immunostimulatory properties of the composition. As used herein, the phrase "substantially contributes" to the immunostimulatory properties of the composition refers to an immunostimulatory effect as described herein.

As used herein, the terms immunostimulatory, immunostimulatory effect or immunostimulatory properties and/or activity relate to the ability of IAvD's in accordance with the invention to cause macrophage activation, and in particular, immunostimulatory activity as indicated by increased expression of NF-kappa Beta directed luciferase expression in THP-1 monocytes as described previously (equal to about 50% that of ELPS at 10 µg/mL at a concentration of 250 µg/mL or less). This may be measured based on any individual *Aloe*-derived component or collection or mixture thereof. Thus, activity can, for example, reflect that of an *Aloe*-derived polysaccharide or its combination with ALP and/or ALPS. A method for measuring this type of macrophage activation, herein incorporated by reference, is disclosed in the '072 patent, column 5, line 12 to column 6, line 22.

Generally, macrophage activation can be measured using a luciferase reporter gene assay in THP-1 human monocytic cells. This assay measures immunostimulatory activity as indicated by increased expression of a NF-kappa Beta-driven luciferase reporter. THP-1 cells are cultured in RPMI 1640 medium supplemented with fetal bovine serum (10% v/v) and amikacin (60 mg/L) at 37° C., under 5% $CO_2$ and 95% air. Actively growing cells are transiently transfected using DEAE-dextran (10 µg/1×$10^6$ cells) and the pBIIXLUC reporter plasmid (1 µg/1×$10^6$ cells) containing two binding sites for NF-kappa Beta. Transfection solution containing THP-1 cells are incubated for 7 minutes in 37° C. water bath. The transfected cells are then resuspended in 10% FBS, RPMI 1640 medium and plated out in 96-well plates at a cell density of 2×$10^5$ cells per well. After 24-hours test samples are added to transfected cells. Four hours after addition of samples, cells are harvested and luciferase activity measured. Cells are harvested using Packard filter plates and lysed using 30 µL of luciferase mix (1:1, LucLite™ luciferase:1×PBS, 1 mM Ca and Mg). Luciferase light emission is measured using a Packard microplate scintillation counter in single photon mode. Activation is reported as a percentage relative to maximal activation of NF-kappa Beta by 10 µg/mL ELPS, used as a positive control. Other assay methods are contemplated.

As used herein, the term non-immunostimulatory *Aloe vera*-derived material and other words indicating this concept are defined as an *Aloe vera*-derived material which does not meet the immunostimulatory requirements of an IAvD as defined herein.

The term *Aloe*-derived lipo-protein or "ALP" refer to bacterial lipo-proteins from bacteria endogenous to *Aloe vera*. This does not mean that the bacteria must come from *Aloe vera* as the bacteria could be separately cultured or cultivated. Gram positive *micrococcus* bacterial species are the most prevalent *Aloe*-associated organisms. These bacteria have evolved to grow well within the *Aloe* plant and do not grow very well in other environments (Waller T A, et al. In *Aloes: The genus Aloe*; Reynolds T, Ed.; CRC Press: NY, 2004; Chapter 8, pp 139-205). Gram positive bacteria contain lipoproteins, but no lipo-polysaccharides. As disclosed herein, lipoproteins are believed to be a significant contributor to in vitro macrophage activation from gram positive bacteria. Since gram positive bacteria are the most prevalent type of bacteria in *Aloe*, lipoproteins represent an important active derived from *Aloe*.

Recent research indicates that consumption of foods containing certain gram positive bacteria can have a beneficial effect on the immune system. This has been most extensively studied with respect to the ingestion of the probiotic lactic acid bacteria *Lactobacillus* and *Bifidobacterium* strains found in yoghurt and similar foods (reviewed in Ezendam and van Loveren, *Nutr Rev.*, 2006, 64: 1-14). Many of these immune enhancing effects do not require viable bacterial cells since they can be mimicked by consumption of heat killed organisms.

As used herein, the terms *Aloe vera* derived lipo-polysaccharide and ALPS refer to a large molecule comprising a lipid and a polysaccharide (carbohydrate) joined by a covalent bond. ALPSs are a major component of the outer membrane of Gram-negative bacteria found in or associated with *Aloe vera*, contributing greatly to the structural integrity of the bacteria, and protecting the membrane from certain kinds of chemical attack. ALPS are endotoxins, and induce a strong response from normal animal immune systems.

LPS generally act as the prototypical endotoxin, because it binds the CD14/TLR4/MD2 receptor complex, which promotes the secretion of pro-inflammatory cytokines in many cell types, but especially in macrophages. An "LPS challenge" in immunology is the exposing of the subject to an LPS which may act as a toxin. LPS also increases the negative charge of the cell membrane and helps stabilize the overall membrane structure. LPS are additionally an exogenous pyrogen (external fever-inducing composition). ALPs are different from ALPSs, also a desirable component of the PLLs of the invention, in that their immunostimulatory action is believed to be mediated through toll-like receptor 2, whereas ALPS are believed to be mediated through toll-like receptor 4.

Some IAvD compositions have no ALPs or ALPSs present that substantially contribute to the immunostimulatory properties of the composition. Other IAvD compositions however, include no polysaccharides, other than ALPSs that substantially contribute to the immunostimulatory properties of the composition. Still other IAvD compositions have only ALPs which substantially contribute to the immunostimulatory properties of the composition.

Preferably, there are two or more of polysaccharides, ALPs and/or ALPSs, any or all of which substantially contribute individually or synergistically to the immunostimulatory activity of the IAvD composition.

Some IAvD compositions include ALPs and/or ALPSs having immunostimulatory activity which are derived from microorganisms such as certain bacteria, yeasts, fungi, molds and the like found in or otherwise associated with *Aloe vera*. These ALPs and ALPSs may also be recovered from microorganisms which have been cultured, so long as that genius and species are found on or associated with *Aloe vera*. These ALPs and ALPSs, which may be found on or within the *Aloe vera* plant, which may be concentrated or synthesized, may be used in addition to, or instead of polysaccharides to provide various benefits in the treatment of, among other things, joint and muscle pain, and enhancing the appearance, texture, firmness, and/or elasticity of skin. PLL's containing *Aloe*-derived polysaccharides, like that described in the '072 patent, as well as both ALPs and APLS's are contemplated for these uses.

As used herein, the term *Aloe*-derived material refers to any material contained in or present on *Aloe vera* including but not limited to *Aloe*-derived polysaccharides, lipo-proteins and lipo-polysaccharides. Such materials can be isolated from the *Aloe* plant and/or synthesized.

As used herein, the term synthetic or synthesized refers to materials which are manmade and/or manufactured and which have the same or similar compositions of those materials found in nature. In the case of ALPs and ALPSs, it also refers to separately cultured.

As used herein, the term "AloeEx" refers to an immunostimulatory PLL mixture, extracted from *Aloe vera* or produced synthetically, comprising the polysaccharide of the '072 patent as well as ALP and ALPS. A PLL such as AloeEX can be isolated from the rind and/or the mucilage of *Aloe vera* leaves (i.e. the region between the inner gel and the outer rind) and may be obtained from *Aloe* waste materials (i.e. spent rinds used in other processes and considered a waste product by current industry standards).

AloeEx often has an immunostimulatory activity, as measured by the techniques described herein, of 5 µg/mL. This means that AloeEx at a concentration of about 5 micrograms/milliliter increases NF-kappa B directed luciferase expression in THP-1 monocytes comparable to levels 50% of those realized by the use of ELPS at a concentration of 10 µg/mL, or more. Of course, batch to batch variations can occur within this level of activity.

As used herein, the term Aloeride (as distinguished from the trademark ALOERIDE® discussed below) refers to an immunostimulatory polysaccharide composition, isolated from *Aloe vera* or produced synthetically, wherein the polysaccharides have an apparent molecular weight greater than about two million daltons and comprise glucose, galactose, mannose and arabinose as reported in the '072 patent. In particular, the Aloeride polysaccharide composition may comprise between about 25% and about 70% glucose, between about 0.5% and 35% rhamnose, between about 5% and about 30% galactose, between about 3% and about 25% mannose and between about 0% and about 15% arabinose (in mole %). In the '072 patent the Aloeride polysaccharide is also called NP18298. For the purpose of the current invention, Aloeride and NP18298 refer to the same composition.

As used herein, the term MagnAloe AG refers to a powdered mixture of *Aloe*-derived polysaccharides having a molecular weight distribution as described at http://www-.firstAloevera.com/magnAloe_information.htm. Any mixture comprising high molecular weight *Aloe*-derived polysaccharide materials is contemplated for the purpose of an IAvD or non-IAvD as described herein.

Preliminary findings leading to the '072 patent suggested that detectable levels of immunostimulation in crude *Aloe* juice and gel could not be accounted for by previously known *Aloe* components. Commercial *Aloe* preparations (200 µg/mL) only resulted in negligible NF-kappa Beta activation in the macrophage assay. Aloeride "NP18298", which accounted for this activity, was found to comprise a polysaccharide-containing fraction where the polysaccharides present had an apparent molecular weight above 2 million daltons. Its major glycosyl components reported therein included glucose, galactose, mannose and arabinose. Based on the degree and methods of purification used and reported in the '072 patent, it is not believed that Aloeride included substantial levels of ALPs and/or ALPSs.

In investigating alternate sources and methods of scaling-up production of Aloeride-containing materials, it was subsequently discovered that other fractions, fractions which could include the fraction described in the '072 patent, along with other materials including ALPs and ALPSs, possessed desirable immunostimulatory activity.

The methods described in the '072 patent, using the starting materials described, provided a relatively pure polysaccharide-containing fraction, devoid of sufficient ALPs and ALPSs to provide significant additional immunostimulatory activity.

Without wishing to be bound by any particular theory of operation, it is believed that ALPS and ALPSs possess separate immunostimulatory properties and may be used in addition to, or instead of polysaccharides to provide various benefits in the treatment of, among other things, joint and muscle pain, and skin elasticity enhancement.

The results of testing indicate that AloeEx which comprises the Aloeride polysaccharide, ALPS and ALPSs, are collectively responsible for the macrophage activation properties (immunostimulatory properties) of AloeEx.

IAvD's may include PLL's, AloeEx, mixtures of ALPs and ALPSs, polysaccharides and the Aloeride polysaccharide (which is substantially free from ALPs and ALPSs). IAvD's may also include other materials, including commercial polysaccharide preparations having immunostimulatory derived compositions and which have been shown to cause activation of NF-kappa Beta directed luciferase expression in THP-1 cells to the extent that they meet the criteria for IAvD's set forth herein.

As stabilized formulations and compositions of IAvD's are desirable, such formulations may include second *Aloe*-derived non-IAvD materials in combination with IAvD materials. Second *Aloe*-derived non-IAvD materials include materials with lower immunostimulatory activity and at least 50% of the polysaccharides generally having a molecular weight of 1,500,000 daltons or less.

If the IAvD is mixed with a second *Aloe*-derived material, whether a second IAvD or non-IAvD, of course, the percentage of individual carbohydrates, and indeed the overall molecular weight can be changed. Moreover, the overall activity of the mixture may change. For example, a mixture of AloeEx and MagnAloe AG 20%:80% mixture will generally have a lower overall molecular weight for the polysaccharides, will have a lower overall activity than AloeEx and will have mannose as the most prevalent carbohydrate.

Non-limiting examples of these second, non-IAvD *Aloe*-derived materials include those selected from the group consisting of MagnAloe AG, *Aloe vera* gel 1× (either natural, ground filet, micronized filet or decolorized), *Aloe vera* gel 10× (either natural or decolorized), *Aloe vera* gel 200× (either dehydrated powder or spray dried powder), *Aloe vera* whole leaf spray dried powder 100×, *Aloe vera* whole leaf decolorized liquid (either 1×, 2×, 4×, or 10×) acemannan, *Aloe vera* mucilaginous polysaccharide (AVMP) and Manapol.

The amount of the second *Aloe*-derived material present in the formulation generally is at least about 10% to about 90% by weight relative to the amount of the total of the second *Aloe*-derived material and the first IAvD. The greater the ability of the second *Aloe*-derived material to solubilize, suspend, emulsify and/or disperse the first IAvD, as well as the greater the activity of the second *Aloe*-derived material, the less that may be needed. In one preferred embodiment, the second *Aloe*-derived material is MagnAloe AG and the amount of MagnAloe AG is greater than the amount of AloeEx, and in a particularly preferred embodiment, they are provided in a 4:1 weight ratio MagnAloe AG to AloeEx. In the resulting homogenous mixture formed by the two, MagnAloe AG would form about 80% thereof. As described and defined herein, MagnAloe AG is not believed to qualify as an IAvD as defined herein.

Other IAvD's and non-IAvD's include commercial polysaccharide preparations such as *Aloe vera* mucilaginous polysaccharide (AVMP) and Manapol, available from Carrington Laboratories Inc. (Irving, Tex.) having immunostimulatory derived compositions and which have been shown to cause activation of NF-kappa Beta directed luciferase expression in THP-1 cells at 200 µg/mL. In particular, AVMP and Manapol are believed to be non-IAvD's having reported activation in the range of 2-4% relative to maximal activation of NF-kappa Beta by 10 µg/mL ELPS.

Any of the abovementioned compositions may be utilized in the present invention either alone or in combination.

Skin Treatment

One aspect of the present invention is a method of improving the appearance, texture, firmness, and/or elasticity of skin or treating decreased skin elasticity in a subject in need thereof. A subject in need thereof is any mammal, particularly, a human, in need of enhanced or improved skin elasticity. This is accomplished by administering to a subject in need thereof an effective amount of an IAvD composition for a period of time sufficient to obtain improvement in the subjects' skin elasticity. Neither improvement nor treatment in accordance with the present invention in the context of skin elasticity requires more than some discernable, measurable improvement therein on a subjective basis. Unless stated otherwise, this can be an improvement for any subject on a subjective basis based on, for example, visual and tactile observation.

However, often improvements are measured based on a statistically significant improvement. As determined by ANOVA, tests as measured by any one of the tests described herein when the methods are utilized with a defined group of subjects to be tested in a clinical study. For example, the Cutometer parameter Ur/Ue describes skin elasticity as it relates to stretching and contracting. Seventy percent of Group 1 subjects showed an improvement in Cutometer parameter Ur/Ue. Relative to baseline, this significant increase in parameter Ur/Ue is equivalent to a 29% improvement at Week 12 for subjects who ingested the invention supplement.

The amount of improvement necessary to achieve statistical significance will be dictated by a number of factors including, without limitation, the number of subjects, the length of the test, the techniques used for measuring improvement in elasticity, the condition of the subject, the type of dosage form, the daily dose used and the like. Moreover, it is not a requirement of the present invention that statistical significance be achieved using each and every testing methodology, so long as it is obtained in at least one test of elasticity.

The IAvD compositions of the invention can be administered through any normal route. However, oral and topical routes, including transdermal routes, are preferred. Of course, the route of administration can dictate much of the design of the dosage forms used to accomplish same.

The amount of IAvD composition found in a single dose will be affected by whether or not it is topically applied or ingested and for what purpose it is used. Generally, however, and irrespective of dosage form selected, the amount of IAvD composition used in accordance with the present invention used for treating skin elasticity ranges from between about 0.0025 mg to about 1 g per day. This means the amount of IAvDs, not the total amount of *Aloe*-derived material. It may not be possible to distinguish the individual components of the IAvD formulations. It is sufficient for these purposes that the IAvDs possess these properties prior to being mixed with other materials.

For example, an IAvD and an *Aloe*-derived non-IAvD may be present or an IAvD may be present.

IAvD formulations for improved skin elasticity may be given as a single dose or as divided doses throughout the day and generally the number of doses given will range from between 1 to about 6 per day, more preferably 1 to 4 per day, most preferably 1 to 2 per day. This is based on an IAvD exhibiting activity characterized by increased NF-kappa B directed luciferase expression in THP-1 cells to levels about 50%, as described herein, of those achieved by ELPS having a concentration of about 10 μg/mL when tested at a concentration of about 5 μg/mL (that generally found in AloeEx). Note that there is variation in this level of monocyte/macrophage activation batch to batch, so more or less PLL may be required to provide an equivalent level of activity. Moreover, other IAvDs may be more or less immunostimulatory when compared to PLL's. An amount of each of these IAvDs that would give comparable activity to PLL's may be needed.

Accordingly, the amount of the IAvD composition found in each dosage form in accordance with the present invention can range from between about 0.0005 milligram to about 1 gram depending upon the daily dose, the number of doses as well as the route of administration.

Most preferably, in terms of improved skin elasticity and/or accelerated skin cell renewal by oral administration, the amount of IAvD composition ranges from between about 0.2 milligram (mg) to about 5 gram (g), more preferably from between about 5 mg to about 1 g, per day most preferably about 10 mg to about 500 mg. And when provided topically the amount ranges from between about 0.0005 mg to about 2.5 mg, more preferably from between about 0.0025 and about 0.25 mg, and even more preferably between about 0.0025 mg to about 0.025 mg. These amounts are based on the use of AloeEx at an activity of about 5 micrograms/milliliter (μg/mL). Amounts of other IAvD's which yield similar results are contemplated.

In a preferred embodiment in accordance with the present invention, the daily dosing of IAvD compositions continue for at least 7 days, more preferably at least 2 weeks, more preferably at least 2 months. Most preferably, the materials of the present invention are administered continuously throughout a subject's life to improve and maintain skin elasticity. However, the amount administered for treatment may, eventually, be reduced to accomplish maintenance of a certain desired level of skin elasticity or accelerated skin cell renewal. Thus, after some period of treatment, once skin elasticity has improved, a lower dose may be administered for maintenance thereof.

When applied topically, the dosage may be spread directly onto an afflicted area. It may in some cases be rubbed into the skin. In other instances, it is not manipulated but is allowed to be absorbed or to remain on the application area as applied. The IAvD may also be applied on occlusive bandage or some other type of wrap placed over it.

Alternatively, the IAvD may be formulated into a patch. These topical applications may be designed to deliver the IAvD to the surface of the skin or to some layer or layers of the skin itself. Alternatively, it may be formulated to deliver the IAvD transdermally for deeper local or systemic distribution. More about the types of materials that can be used to formulate oral and topical dosage forms are discussed herein.

When administered orally, IAvD compositions may be provided in a tablet, capsule, powder, sachet, lozenge, gum candy or any other ingestible form. The IAvD may also be provided as a liquid or as a solid which is first dissolved in or mixed with a liquid before ingestion. Dosage forms may be swallowable or may be solids in the mouth and disintegrate in the mouth prior to ingestion. The IAvD may even be sprinkled on food and ingested therewith.

Note that "accelerated cell regeneration" is an end point in its own right and methods of enhancing accelerated cell regeneration and products which accomplish this using IAvD compositions are also contemplated. Accelerated cell regeneration is the regeneration of skin cells under dead layers of skin which are desirably exfoliated. This is accomplished using the same techniques and products as described in connection with skin elasticity.

Joint/Muscle Pain

Another aspect of the present invention is the improvement or the treatment of joint and/or muscle pain in subjects in need thereof by the use of IAvD compositions in accordance with the present invention. Generally, the routes of administration and dosage forms previously discussed in accordance with skin elasticity apply equally well to these methods. Topical application can affect a particular muscle or muscle group and/or a particular joint. Systemic administration (orally or transdermally) may reduce pain at that same location and/or may provide broader relief over many muscle groups and/or joints.

Also as noted previously in connection with skin elasticity, treatment in accordance with this aspect of the present invention means a reduction in joint pain and/or muscle pain which can be measured subjectively on a subject-by-subject basis. However, more preferably, a successful product in accordance with the present invention will provide adequate treatment in a statistically significant way when given to a group of subjects treated over an extended period of time. Desirably, at least 75% of subjects will manifest a lower frequency of muscle and/or joint pain, a reduction in pain intensity or a reduction in pain duration after twelve weeks of treatment. This can be pain generally or in a specific muscle or joint.

Improvement in a subject's condition in the context of joint pain and/or muscle pain is often determined by a subjective rating system scored by each individual rating his or her pain at a specific site or generally before, during and/or after treatment.

Also as previously noted, the amount of IAvD composition administered in accordance with this aspect of the present invention will vary depending upon the route of administration, the area to be treated, the degree and type of pain and the like. However, the amount generally will be in the same ranges as previously described in connection with the methods of improving skin elasticity. It is also possible in both this method and methods of improving skin elasticity to administer the IAvD composition both orally and topically at the same time or within the same day, or on some alternative or complementary schedule thereby providing both general and more specifically targeted relief or improvement.

Any IAvD composition may be used in accordance with the present invention. For example, any PLL, any AloeEx or any Aloeride polysaccharide formulation exhibiting immunostimulatory properties as described herein may be used. The present invention includes pharmaceutical compositions and methods of using an IAvD, optionally in combination with acceptable pharmaceutical carriers or excipients.

Compositions

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

The amount of the composition administered will be dependent upon the condition being treated, the subject being treated, on the subject's weight, the severity of the affliction, the manner of administration and the judgment of the individual's physician or of the individual.

As discussed above, suitable routes of administration may, for example, include oral, transmucosal, topical or transdermal.

The pharmaceutical compositions of the present invention may be manufactured in a manner that is itself known, e.g., by means of conventional mixing, dissolving, granulating, dragee-making, powderizing, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the compositions and compounds into preparations which can be used pharmaceutically. Proper formulation is dependent upon the route of administration chosen.

For oral administration, the compositions can be administered alone or formulated readily by combining the active compositions with pharmaceutically acceptable carriers well known in the art. Such carriers enable the compositions of the invention to be formulated as tablets, pills, dragees, capsules, liquids, gels, syrups, slurries, suspensions and the like, for oral ingestion by a patient to be treated.

Pharmaceutical preparations for oral and/or topical use can be obtained using a solid excipient, optionally grinding or milling the individual components of a preparation and/or a resulting mixture, and processing the components and/or mixture of granules, after adding suitable auxiliaries, if desired, to obtain for example, creams, lotions, serums, powders, effervescent formulations, tablets or dragee cores. Granulation is, however, but one of numerous known techniques which may be used.

Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

If desired, disintegrating agents may be added, such as PVP, sodium starch glycolate, cross-linked polyvinyl pyrrolidone, agar, or alginic acide or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active composition doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compositions may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner.

For topical administration, emulsions, microemulsions, or other topical creams, lotions, milks, washes, ointments, serums or gels may also be prepared. Direct emulsification of AloeEx may be possible, for example preparation of an AloeEx oil-in-water emulsion wherein the hydrophobic core or an oil phase is largely composed of AloeEx. Other surfactants or formulary excipients may be added to physically stabilize the emulsion.

Pharmaceutical preparations suitable for topical administration are especially creams, ointments and gels and also pastes, foams, tinctures and solutions that contain from approximately 0.05 to approximately 5% IAvD composition by weight. Preferably the preparations are about 0.5% IAvD composition by weight. These compositions include the total amount of *Aloe*-derived materials including, as appropriate, at least one IAvD and any other *Aloe* based materials. In the formulations discussed in the clinical studies, for example the 0.5% IAvD composition was made up of a 1:4 mixture of AloeEx and MagnAloe AG.

Creams or lotions may be oil-in-water emulsions that typically contain more than 50% water. As oily base there are used especially fatty alcohols, especially those containing from 12 to 18 carbon atoms, for example lauryl, cetyl or stearyl alcohol, fatty acids, especially those containing from 10 to 18 carbon atoms, for example palmitic or stearic acid, liquid to solid waxes, for example isopropyl myristate, wool wax or beeswax, and/or hydrocarbons, especially liquid, semi-solid or solid substances or mixtures thereof, for example petroleum jelly (petrolatum) or paraffin oil. Suitable emulsifiers are surface-active substances having predominantly hydrophilic properties, such as corresponding non-ionic emulsifiers, for example fatty acid esters of polyalcohols or ethylene oxide adducts thereof, especially corresponding fatty acid esters with (poly)ethylene glycol, (poly)propylene glycol or sorbitol, the fatty acid moiety containing especially from 10 to 18 carbon atoms, especially partial glycerol fatty acid esters or partial fatty acid esters of polyhydroxyethylene sorbitan, such as polyglycerol fatty acid esters or polyoxyethylene sorbitan fatty acid esters (Tweens), and also polyoxyethylene fatty alcohol ethers or fatty acid esters, the fatty alcohol moiety containing especially from 12 to 18 carbon atoms and the fatty acid moiety especially from 10 to 18 carbon atoms, especially those having approximately from 2 to 23 ethylene glycol or ethylene oxide units, such as polyhydroxyethylenecetyl-stearyl ether (for example Cetomacrogol), polyhydroxyethylene-(4)-lauryl ether and polyhydroxyethyleneglycerol fatty acid ester (for example Tagat S), or corresponding ionic emulsifiers, such as alkali metal salts of fatty alcohol sulfates, especially having from 12 to 18 carbon atoms in the fatty alcohol moiety, for example sodium lauryl sulfate, sodium cetyl sulfate or sodium stearyl sulfate, which are usually used in the presence of fatty alcohols, for example cetyl alcohol or stearyl alcohol.

Additives to the aqueous phase are agents that prevent the creams from drying out, for example humectants, such as polyalcohols, such as glycerol, sorbitol, propylene glycol and/or polyethylene glycols, and also preservatives, perfumes, etc.

Ointments or lotions may be water-in-oil emulsions that typically contain up to 70%, but preferably from approximately 20% to approximately 50%, water or aqueous phase. Suitable as fatty phase are especially hydrocarbons, for example petroleum jelly, paraffin oil and/or hard paraffins, which, in order to improve the water-binding capacity, preferably contain suitable hydroxy compounds, such as fatty alcohols or esters thereof, for example cetyl alcohol or wool wax alcohols, or wool wax.

Emulsifiers are corresponding lipophilic substances, such as sorbitan fatty acid esters (Spans), for example sorbitan oleate and/or sorbitan isostearate. Additives to the aqueous phase are, inter alia, humectants, such as polyalcohols, for example glycerol, propylene glycol, sorbitol and/or polyethylene glycol, and also preservatives, perfumes, etc.

Microemulsions are isotropic systems based on the following four components: water, an emulsifier, for example of the type indicated above, such as a surfactant, for example emulgin, a lipid, such as a non-polar oil, for example paraffin oil, and an alcohol containing a lipophilic group, for example 2-octyldodecanol. If desired, other additives may be added to the microemulsions.

Fatty ointments are water-free and contain as base especially hydrocarbons, for example paraffin, petroleum jelly and/or liquid paraffins, also natural or partially synthetic fat, such as fatty acid esters of glycerol, for example coconut fatty acid triglyceride, or preferably hardened oils, for example hydrogenated groundnut oil or castor oil, also fatty acid partial esters of glycerol, for example glycerol mono- and di-stearate, and also, for example, the fatty alcohols increasing the water-absorption capacity, emulsifiers and/or additives mentioned in connection with the ointments.

With gels, a distinction is made between aqueous gels, water-free gels and gels having a low water content, which gels consist of swellable, gel-forming materials. There are used especially transparent hydrogels based on inorganic or organic macromolecules. High molecular weight inorganic components having gel-forming properties are predominantly water-containing silicates, such as aluminium silicates, for example bentonite, magnesium aluminium silicates, for example Veegum, or colloidal silicic acid, for example Aerosil. As high molecular weight organic substances there are used, for example, natural, semi-synthetic or synthetic macromolecules. Natural and semi-synthetic polymers are derived, for example, from polysaccharides containing a great variety of carbohydrate components, such as celluloses, starches, tragacanth, gum arabic and agar-agar, and gelatin, alginic acid and salts thereof, for example sodium alginate, and derivatives thereof, such as lower alkylcelluloses, for example methyl- or ethyl-cellulose, carboxy- or hydroxy-lower alkylcelluloses, for example carboxymethyl- or hydroxyethyl-cellulose. The components of synthetic gel-forming macromolecules are, for example, suitably substituted unsaturated aliphatic compounds such as vinyl alcohol, vinylpyrrolidine, acrylic or methacrylic acid. Examples of such polymers are polyvinyl alcohol derivatives, such as polyviol, polyvinylpyrrolidines, such as collidone, polyacrylates and polymethacrylates, especially having a molecular weight of from approximately 80,000 to approximately 1 million, or salts thereof, such as Rohagit S, Eudispert or Carbopol. Customary additives, such as preservatives, stabilizers, or perfumes, may be added to the gels.

Foams are administered, for example, from pressurized containers and are liquid oil-in-water emulsions in aerosol form; unsubstituted or halogenated hydrocarbons, such as alkanes, for example propane or butane, or chlorofluoro-lower alkanes, for example dichlorodifluoromethane and dichlorotetrafluoroethane, are used as propellant. As oil phase there are used, inter alia, hydrocarbons, for example paraffin oil, fatty alcohols, for example cetyl alcohol, fatty acid esters, for example isopropyl myristate, and/or other waxes. As emulsifiers there are used, inter alia, mixtures of emulsifiers having predominantly hydrophilic properties, such as polyoxyethylene sorbitan fatty acid esters, and emulsifiers having predominantly lipophilic properties, such as sorbitan fatty acid esters. The customary additives, such as preservatives, etc., are also added.

Tinctures and solutions generally have an ethanolic base, to which water may be added and to which there are added, inter alia, polyalcohols, for example glycerol, glycols and/or polyethylene glycol, as humectants for reducing evaporation, and fat-restoring substances, such as fatty acid esters with low molecular weight polyethylene glycols, that is to say lipophilic substances that are soluble in the aqueous mixture, as a replacement for the fatty substances removed from the skin by the ethanol, and, if necessary, other adjuncts and additives. Suitable tinctures or solutions may also be applied in spray form by means of suitable devices.

The manufacture of the topically administrable pharmaceutical preparations is effected in a manner known per se, for example by dissolving or suspending the active ingredient in the base or, if necessary, in a portion thereof. When the active ingredient is administered in the form of a solution, it is generally dissolved in one of the two phases before emulsification; when the active ingredient is administered in the form of a suspension, it is mixed with a portion of the base after emulsification and then added to the remainder of the formulation.

An IAvD composition or combination of IAvD compositions may by applied as a topical medication for local effect, such as enhanced skin elasticity and/or accelerated skin cell growth or regeneration. This is a treatment which is applied to the skin and acts directly at the site of application. It must be placed at the site of pathology, and it directly absorbs through the skin and exerts its effect. It is believed that there is no systemic absorption needed for the effect to occur.

An IAvD composition or combination of IAvD compositions may be applied as a topical medication for systemic effect. This is a treatment which is applied to the skin and acts at a site distant from the site of application to reduce muscle or joint pain, enhance skin elasticity or both. The medication may be applied anywhere on the body and achieve its effect. The formulation must absorb through the skin, enter the bloodstream, reach effective levels in the blood, and then travel to its site of action to exert its effect.

It will be known to persons of ordinary skill in the art that skin penetration enhancers may be used to facilitate systemic delivery of the IAvD composition or compositions or even deeper muscle or joint penetration. In this regard, penetration enhancers have been used to increase the permeability of the dermal surface to drugs, and are often proton accepting solvents such as dimethyl sulfoxide (DMSO) and dimethylacetamide. Other penetration enhancers that have been studied and reported as effective include 2-pyrrolidine, N,N-diethyl-m-toluamide (Deet), 1-dodecal-azacycloheptane-2-one N,N-dimethylformamide, N-methyl-2-pyrrolidine, calcium thioglycolate, hexanol, fatty acids and esters, pyrrolidone derivatives, derivatives of 1,3-dioxanes and 1,3-dioxolanes, 1-N-dodecyl-2-pyrrolidone-5-carboxylic acid, 2-pentyl-2-oxo-pyrrolidineacetic acid, 2-dodecyl-2-oxo-1-pyrrolidineacetic acid, 1-azacycloheptan-2-one-2-dodecylacetic acid, and aminoalcohol derivatives, including derivatives of 1,3-dioxanes, among many others.

An IAvD composition or combination of IAvD compositions may be included in dosage forms used to treat any responsive condition, such as, joint pain, muscle pain, loss of skin elasticity or skin wrinkles.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Stable compositions for treatment, prevention, or amelioration of any of the conditions, diseases, afflictions, wounds and the like, including, without limitation one or more symptoms of joint or muscle pain and for enhancing skin elasticity are provided. The compositions provided herein are stable formulations of an immunostimulatory Aloe vera extract or a derivative thereof, in a pharmacologically suitable fluid that are stable during long term storage. The compositions are may be suitable for direct administration to a subject in need thereof or may be in a concentrated form. Pharmacologically suitable fluids include, but are not limited to, polar fluids, including protic fluids. In certain embodiments herein, the compositions are aqueous solutions. In other embodiments, the compositions are non aqueous or emulsions.

The IAvD compositions may be formulated with a pharmacologically suitable fluid or solvent. Pharmacologically suitable fluids include, but are not limited to, polar solvents, including, but not limited to, compounds that contain hydroxyl groups or other polar groups. Such solvents include, but are not limited to, water or alcohols, such as ethanol, isopropanol, and glycols including propylene glycol, polyethylene glycol, polypropyleneglycol, glycol ether, glycerol and polyoxyethylene alcohols.

Polar solvents also include protic solvents, including, but not limited to, water, aqueous saline solutions with one or more pharmaceutically acceptable salt(s), alcohols, glycols or a mixture thereof. For a saline solution as the solvent or as a component thereof, particularly suitable salts are those which display no or only negligible pharmacological activity after administration.

The compositions provided herein also may include excipients and additives. The particular excipient or additive for use in the compositions for long term storage provided herein may be determined empirically using methods well known to those of skill in the art. Excipients and additives are any pharmacologically suitable and therapeutically useful substance which is not an active substance. Excipients and additives generally have no pharmacological activity, or at least no undesirable pharmacological activity. The excipients and additives include, but are not limited to, surfactants, stabilizers, complexing agents, antioxidants, or preservatives which prolong the duration of use of the finished pharmaceutical formulation, flavorings, vitamins, or other additives known in the art.

Complexing agents include, but are not limited to, ethylenediaminetetraacetic acid (EDTA) or a salt thereof, such as the disodium salt, citric acid, nitrilotriacetic acid and the salts thereof. In one embodiment, the complexing agent is EDTA. Preservatives include, but are not limited to, those that protect the solution from contamination with pathogenic particles, including benzalkonium chloride or benzoic acid, or benzoates such as sodium benzoate. Antioxidants include, but are not limited to, vitamins, provitamins, ascorbic acid, vitamin E or salts or esters thereof.

The compositions provided herein also may include a cosolvent, which increases the solubility of additives or the active ingredient(s). The particular cosolvent for use in the compositions for long term storage provided herein may be determined empirically using methods well known to those of skill in the art. Cosolvents for use herein include, but are not limited to, hydroxylated solvents or other polar solvents, such as alcohols such as isopropyl alcohol, glycols such as propylene glycol, polyethylene glycol, polypropylene glycol, glycol ether, glycerol, and polyoxyethylene alcohols.

In other of embodiments, the compositions further contain a buffer, including, but not limited to, citric acid/phosphate, acetate, barbital, borate, Britton-Robinson, cacodylate, citrate, collidine, formate, maleate, McIlvaine, phFosphate, Prideaux-Ward, succinate, citrate-phosphate-borate (Teorell-Stanhagen), veronal acetate, MES (2-(N-morpholino) ethanesulfonic acid), BIS-TRIS (bis(2-hydroxyethyl)imino-tris-(hydroxymethyl)methane), ADA (N-(2-acetamido)-2-iminodiacetic acid), ACES (N-(carbamoylmethyl)-2-aminoethanesulfonic acid), PIPES (piperazine-N,N'-bis(2-ethanesulfonic acid)), MOPSO (3-(N-morpholino)-2-hydroxypropanesulfonic acid), BISTRIS PROPANE (1,3-bis(tris(hydroxymethyl)methylamino)propane), BES (N,N-bis(2-hydroxyethyl)-2-aminoethanesulfonic acid), MOPS (3-(N-morpholino)propanesulfonic acid), TES (N-tris(hydroxymethyl)methyl-2-aminoethanesulfonic acid), HEPES (N-(2-hydroxyethyl)piperazine-N'-(2-eth-anesulfonic acid), DIPSO (3-(N,N-bis(2-hydroxyethyl)amino)-2-hydroxypropan-esulfonic acid), MOBS (4-(N-morpholino)-butanesulfonic acid), TAPSO (3-(N-tris(hydroxymethyl)methyl-amino)-2-hydroxypropanesulfonic acid), TRIZMA® (tris (hydroxymethylaminomethane), HEPPSO(N-(2-hydroxyethyl)piperazine-N'-(2-hydroxypropanesulfonic acid), POPSO (piperazine-N,N'-bis(2-hydroxypropanesulfonic acid)), TEA (triethanolamine), EPPS (N-(2-hydroxyethyl)piperazine-N'-(3-propanesulfon-ic acid), TRICINE (N-tris(hydroxy-methyl)methylglycine), GLY-GLY (glycyl-glycine), BICINE (N,N-bis(2-hydroxyethyl)glycine), HEPES (N-(2-hydroxyethyl)piperazine-N'-(4-butanesulfonic acid)), TAPS(N-tris(hydroxymethyl)methyl-3-aminopropanesulfonic acid), AMPD (2-amino-2-methyl-1,3-propanediol), and/or any other buffers known to those of skill in the art.

The particular buffer and buffer concentration of a given composition provided herein may be determined empirically using standard stability assays well known to those of skill in the art.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a composition of the invention formulated in a compatible pharmaceutical carrier may also be prepared, placed in an appropriate container, and labeled for treatment of an indicated condition. Suitable conditions indicated on the label may include treatment of a condition.

The formulation may also contain optional ingredients including, for example, herbs, vitamins, minerals, enhancers, colorants, sweeteners, flavorants, inert ingredients, and the like. Such optional ingredients may be either naturally occurring or concentrated forms. Selection of one or several of these ingredients is a matter of formulation, design, consumer preference and end-user.

In accordance with another aspect of the present invention, various materials have been found which can be used to allow for the production of a homogenous dispersion, emulsion, suspension, solution and the like of an IAvD. In particular, it has been found that certain highly active, but generally insoluble IAvDs can be dispersed, suspended, emulsified and/or solubilized by using a second *Aloe*-derived material. That second *Aloe*-derived material may be a second IAvD or a material which has insufficient activity to qualify as an IAvD. The amount of the second *Aloe*-derived material should be an amount which is sufficient to allow for, as desired, the production of a homogenous dispersion, solution, homogeneous suspension, or homogeneous emulsion of the first IAvD. Generally at least about 10% of the second *Aloe*-derived material is required, by weight percent, relative to the weight percent of the total weight of the first IAvD and the second *Aloe*-derived material.

In a particularly preferred embodiment in accordance with the present invention, the first IAvD is AloeEx. Any *Aloe*-derived material that can improve the processability of the first IAvD may be used. The second *Aloe*-derived material generally is composed of polysaccharides in which at least 50% of the polysaccharides have molecular weights of 1,500,000 daltons or less. This second *Aloe*-derived material, can include, without limitation, an *Aloe* based material selected from the group consisting of MagnAloe AG, *Aloe vera* gel 1× (either natural, ground filet, micronized filet or decolorized), *Aloe vera* gel 10× (either natural or decolorized), *Aloe vera* gel 200× (either dehydrated powder or spray dried powder), *Aloe vera* whole leaf spray dried powder 100×, *Aloe vera* whole leaf decolorized liquid (either 1×, 2×, 4×, or 10×), acemannan, *Aloe vera* mucilaginous polysaccharide (AVMP) and Manapol. MagnAloe AG is a powder available from First *Aloe* of Costa Rica, S.A. Information can be obtained at www.firstAloevera.com/magnAloe_information.htm. MagnAloe AG has polysaccharide levels of over 800 kiladaltons (KDa) as indicated below. This is on average 40% higher than spray dried 200-1 *Aloe vera* powder sold on the market. MagnAloe AG is reported to contain 42.65 mg/g of polysaccharides having a molecular weight (MW) of 50-200 KDa, 118.5 mg/g having a MW of 200-800 KDa, 366.2 mg/g having a MW 800-1400 KDa, 155.8 mg/g having a MW 1400-2000 KDa of a total polysaccharide of 683.1 mg/g. The water solubility of the MagnAloe generally is about 15%.

*Aloe vera* gel 1× (either natural, ground filet, micronized filet or decolorized), *Aloe vera* gel 10× (either natural or decolorized), *Aloe vera* gel 200× (either dehydrated powder or spray dried powder), *Aloe vera* whole leaf spray dried powder 100×, *Aloe vera* whole leaf decolorized liquid (either 1×, 2×, 4×, or 10×) are available for Improve USA, Inc., 215 Dalton Drive, Suite D, DeSoto, Tex. 75115. The water solubility of *Aloe vera* gel 200× generally is about 90-100%.

Acemannan, *Aloe vera* mucilaginous polysaccharide (AVMP) and Manapol are available from Carrington Laboratories, Irving, Tex. In one particularly preferred embodiment, the single most prevalent carbohydrate in the IAvD is glucose, and the single most prevalent carbohydrate in the second *Aloe*-derived material is mannose.

In one embodiment, the amount of the first IAvD ranges from about 10% to about 90% by weight based on the total amount of the first IAvD and second *Aloe*-derived material and the amount of the second material ranges from about 90% to about 10% based on the amount of the first IAvD and second *Aloe*-derived material. In one preferred embodiment, the amount of the second material is greater than the amount of the first IAvD, and in a particularly preferred embodiment, they are provided in a 4:1 weight ratio second material to first IAvD. In the resulting homogenous mixture formed by the two, the second material would form about 80% thereof. In still another preferred aspect, the first IAvD is AloeEx and the second material is an *Aloe*-derived material that includes polysaccharides in which at least 50% of the polysaccharide have molecular weights of about 1,500,000 daltons or less, such as MagnAloe AG and the amount of the AloeEx ranges from about 10% to about 90% by weight based on the amount of the AloeEx and MagnAloe and the amount of the MagnAloe AG ranges from about 90% to about 10% based on the amount of the AloeEx and MagnAloe AG. In one preferred embodiment, the amount of the MagnAloe AG is greater than the amount of the AloeEx, and in a particularly preferred embodiment, they are provided in a 4:1 weight ratio MagnAloe AG to AloeEx. In the resulting homogenous mixture formed by the two, the MagnAloe AG would form about 80% thereof.

In one embodiment, AloeEx and a second material, preferably a second *Aloe*-derived material may be formulated by mixing raw AloeEx with water which has been heated to approximately 80° C. The mixture is agitated for at least 10 minutes to homogenize the material. The mixture is then filtered, preferably with a filter having a pore size no larger than 15 microns. The resulting filtrate may be utilized in formulating a variety of IAvD compositions as described herein.

Homogenization of AloeEx may or may not require heat depending on the equipment utilized. For example homogenizers may be used as part of the process to render a uniform particulate suspension. A commonly known "color" homogenizer may be used to reduce AloeEx particle size to formulate an aqueous AloeEx suspension and/or emulsion.

A characterization of AloeEx is shown in FIG. 1. The material forms a brown to green flaked powder.

Referring to FIG. 1, a chart depicts one lot of AloeEx material (batch 56) with associated sugar content based on the mole % of total carbohydrates.

FIG. 1 shows the results of glycosyl composition analysis performed by The University of Georgia, Complex Carbohydrate Research Center by combined gas chromatography/ mass spectrometry (GC/MS) of the per-O-trimethylsilyl (TMS) derivatives of the monosaccharide methyl glycosides produced from the sample by acidic methanolysis.

Methyl glycosides were first prepared from a dry sample provided by the inventors by methanolysis in 1 M HCl in methanol at 80° C. (18-22 hours), followed by re-N-acetylation with pyridine and acetic anhydride in methanol (for detection of amino sugars). The samples were then per-O-trimethylsilylated by treatment with Tri-Sil (Pierce) at 80° C. (0.5 hours). [These procedures were carried out as previously described in Merkle and Poppe (1994) *Methods Enzymol.* 230:1-15; York, et al. (1985) *Methods Enzymol.* 118:3-40.] A significant level of precipitate was noted immediately upon addition of Tri Sil. GC/MS analysis of the TMS methyl glycosides was performed on an HP 5890 GC interfaced to a 5970 MSD, using an All Tech EC-1 fused silica capillary column (30 m×0.25 mm ID).

The monosaccharides were identified by their retention times in comparison to standards, and the carbohydrate character of these were authenticated by their mass spectra. For interpreting the mass spectral data, fragment ion 73 is the characteristic base fragment for all TMS methyl glycosides, 204 and 217 are characteristic of neutral sugars, and 173 is characteristic of amino sugars. Fragment 217 is also characteristic of uronic acids and fragment ion 298 is characteristic of the sialic acids.

FIG. 1 identifies the glcosyl residue composition by mole %. Values are expressed as mole percent of total carbohydrate. The total percent carbohydrate was calculated to be 8.6%. The constituent values measured were glucose 61.1%, arabinose 9.5%, galactose 9.2%, galacturonic acid 7.9%, mannose 6.6%, xylose 1.6%, ribose 1.5%, rhamnose 1.4% and fucose 1.1%.

Clinical Study—Skin Elasticity—Topical Formulation

One clinical study, as outlined below demonstrates the effect of one IAvD composition, sold under the trademark ALOERIDE®. ALOERIDE® may be administered topically to improve skin elasticity and may also be used as an ingredient in a nutritional supplement.

The effect of an ALOERIDE® gel 0.5% Product #10849LL, Lot #11939 on skin elasticity or firmness, was determined in a clinical study by Consumer Product Testing, Inc. of Fairfield, N.J. The test formulation (ALOERIDE® gel 0.5%) comprised a 4:1 mixture by weight of MagnAloe AG and AloeEx and was mixed with water, alcohol (10%) and a small amount of Carbopol (0.5%) then dispersed using a homogenizer. The dispersion of AloeEx, water, alcohol and a small amount of carbopol was used to make up the test gel suspension.

The test product was supplied in small containers sufficient to last for 8 weeks when applied to defined facial areas (alcohol performs as a preservative).

The clinical trial was a double test of AloeEx function: Carbopol tends to be drying, a negative test performance factor estimated at (−) 15%. The clinical trial proved the ability of AloeEx/MagnAloe AG to: 1) Reduce fine lines and wrinkles in a statistical majority of the test subjects at 4 weeks and at 8 weeks; 2) The ability of AloeEx to overcome any negative dryness associated with carbopol.

AloeEx used in this clinical trial was non-dispersible/insoluble and difficult to homogenize. When mixed 1:4 with MagnAloe AG, however, a homogenous gel/emulsion was realized.

Thirty-one qualified male and female subjects, ranging in age from 40 to 65 years, were selected for study. The test material indicated a significant reduction in skin rebound time at both the 4 week and 8 week evaluation intervals. Study participants experience up to a 72% improvement in skin elasticity or firmness at the conclusion of the study (FIG. 2) and 100% of the study participants experienced general improvement in skin elasticity. Study demographics based on age and gender are shown in FIG. 3.

Subjects reported to the laboratory with cleansed faces of the first day of testing for a base measurement. Prior to conducting any readings or scoring, subject equilibrated in an environmentally controlled room for 15 minutes at ambient conditions; temperature at 21° C.+/−2° C.; relative humidity at 40%+/−2%.

Skin elasticity (firmness) was measured using the pinch test as disclosed by Shanahan. R. W., et al, Parameters for Assessing the Efficacy of Skin Care Products. Drug & Cosmetic Industry, 140, No. 1, 42-48, 1987. Skin elasticity or firmness scores were obtained by an expert tester by grasping the skin of the lateral, suborbital area of the eyes between thumb and forefinger. The resultant folds were released and timing of all visible movement of the skin, from release until no further motion, was observed and measured to the nearest one hundredth of a second. Scores were recorded on a Data Recording form for statistical analysis of the measurements.

Improvements in skin elasticity are considered substantiated if the is a statistically significant (P less than or equal to 0.05 using the dependent t-Test) decrease in the mean score between the baseline measurements and the subsequent 4 week and 8 weeks post treatment scoring intervals.

FIG. 2 shows a statistically significant decrease in mean skin rebound time in seconds (an indicator of an increase in skin elasticity or firmness). The mean of all baseline measurements was 2.09 seconds and 1.96 seconds for left and right measurements respectively. A significant decrease was observed at the week 4 test interval yielding 1.60 seconds and 1.53 seconds respectively. Further decreases in mean skin rebound time to 1.19 seconds and 1.18 seconds, for left and right, were measured at the week 8 test interval. As previously discussed, the results were statistically significant as p was calculated to be less than or equal to zero for all measurement intervals (FIG. 2).

Another clinical study, as outlined below demonstrates the effect of another IAvD composition administered orally to improve muscle and/or joint pain and skin elasticity.

Clinical Study—Skin Elasticity—Joint/Muscle Pain—Oral Formulation

A study was conducted by Clinical Research Laboratories, Inc. to evaluate the efficacy of an oral supplement of the instant invention designed to improve skin firmness and elasticity and to diminish muscle and joint pain during a 12-week period. (A Double-Blind Placebo Controlled Pilot Study to Assess the Safety and Efficacy of an Oral Supplement Designed to Diminish Aging, study number CRL34706 herein incorporated by reference in its entirety). Placebo tablets used in this clinical study contained microcrystalline cellulose, croscarmellose sodium, stearic acid, silicon dioxide, and magnesium stearate. The active tablets contained the same inactive ingredients as the placebo tablets with 50 mg of a 4:1 mixture of MagnAloe AG and AloeEx. These tablets were given twice daily, orally, at the time of arising and once at bedtime.

This study was initiated on Aug. 30, 2006 and was completed on Dec. 15, 2006. Initially, safety screening was performed as follows on each subject.

Safety Evaluations Blood Analysis

Blood was drawn from each subject at designated study visits, and the following blood tests were performed:

Complete Blood Count (CBC) with differential and platelet count.

Chemistry Panel+HDL AST (GOT), ALT (GPT), gamma Gt, LDH (LD), Total Protein (TP), Uric Acid, (UA, total Billirubin, Urea Nitrogen (UN), total cholesterol (HDL, LDL, TG), Na, K, Ca, Cl.

Urine Analysis

A urine specimen was obtained from each subject at designated study visits, and the following urine tests were performed:

Glucose, Protein, Uribilinogen, Blood, pH

Sitting Vital Signs

An assessment of sitting vital signs (i.e., pulse, blood pressure and respirations) was recorded at the screening visit.

Pregnancy Test

All panelists (with the exception of post-menopausal women) were given a urine pregnancy test at the screening visit.

Dermal Evaluations

In order to determine the effects of treatment on the skin, a CRL Technician performed dermal evaluations on each subject's face to examine for the presence of erythema, edema and dryness. The extent and/or severity of evidence of dermal irritation was recorded utilizing the following scoring scale:

Scoring Scale For Erythema, Edema and Dryness

0=None 1=Mild 2=Moderate 3=Severe

Efficacy Evaluations

Cutometer

The suction is generated by a variable vacuum pump, and the depth of penetration of the skin into the probe is measured optically with an accuracy of 0.01 mm. The probe is attached to a computer, which controls the vacuum application and plots skin deformation as a function of time. From the resulting curve, a number of variables can be extrapolated including immediate, delayed and final distention and immediate retraction (Elsner 1990).

These variables estimate the elastic, viscoelastic and purely viscous behavior of the skin (Barel et al. 1995).

The following parameters were measured:

The final distention, Uf, measured at 10 seconds. The immediate distention, Ue, measured at 0.1 seconds. The delayed distention, Uv. Immediate retraction, Ur The deformation parameters are extrinsic parameters dependent on skin thickness.

In order to circumvent the measurement of skin thickness, the following ratios were used to evaluate the elastic nature of the skin (Elsner 1990, Cua et al. 1990, Krushe and Wonet 1995 and Dobrev 1995):

Ur/Ue is the biological elasticity of the skin. It measures the ability of the skin to regain its initial configuration after deformation. A value of 1 indicates 100% elasticity.

Uv/Ue is the ratio between delayed and immediate deformation, i.e., it is the viscoelastic to elastic ratio. An increase in the value of this ratio indicates that there has been an increase in the viscoelastic portion of the deformation and/or relative decrease of the elastic part.

Ur/Uf is a measure of the net elasticity of the skin.

This study consisted of a pre-screening visit, during which time subjects were examined by a Clinical Research Technician to determine eligibility. Eligible subjects exhibited mild to moderate fine lines and wrinkles on the crow's feet area of the face and experienced chronic muscle and/or joint pain. At this time, subjects were informed not to eat or drink anything after 9:00 p.m. on the evening prior to the scheduled screening visit, in preparation for the blood and urine analysis.

Prior to study initiation, subjects arrived at the CRL laboratory for the scheduled screening visit. Blood was drawn from each perspective subject and the forearm utilized for blood collection was recorded on a case report form. A urine specimen was obtained from each panelist for urine analysis, an assessment of sitting vital signs (i.e., pulse, blood pressure and respirations) was performed and recorded, and all panelists (with the exception of pre-menopausal subjects) were given a urine pregnancy test. Subjects discontinued the use of all oral supplements for the remainder of the conditioning period and for the duration of the study, with the exception of the oral supplements provided to each subject during the study.

To standardize the skin condition of the study population at baseline and minimize variability attributable to use of different skin care regimens, a one week conditioning period began the study. Subjects were required to undergo a one week conditioning period, during which time a glycerin soap was used for all facial washing prior to study initiation. At the screening visit, each subject was provided with detailed study instructions, a bar of glycerin soap to use for all facial washing, Cetaphil® Daily Facial Moisturizer SPF 15 to use once per day, and a Daily Diary to record soap usage and verify compliance. Subjects began cleansing the face with the soap twice daily (morning and night), beginning seven days prior to the baseline visit. At this screening visit, every subject completed a screening questionnaire.

Qualified subjects had normal blood and urine test results and each panelist's vital signs were within the normal range, as a result of the previously mentioned screening visit safety evaluations. Additionally, eligible subjects who agreed to follow-up visits and study requirements and met all of the Inclusion/Exclusion Criteria, were to be impaneled for the study.

Upon returning to the CRL testing facility for the baseline visit, subjects acclimated to ambient laboratory conditions for a period of 30 minutes prior to evaluations. Following the acclimation period, a dermal evaluation of the face of each subject was performed by a trained CRL Technician, for the presence of erythema, edema and dryness. For each subject, either the right or the left side of the face was selected for measurement, as determined by a computer-generated randomization code (FIG. 4). Measurement designation remained consistent throughout the study. Cutometer readings were captured from the cheekbone region below the eye on the same side of the face. All measurements were appropriately recorded. Each subject completed a baseline consumer perception questionnaire in order to evaluate the type and frequency of muscle and joint pain.

A specified test material was randomly assigned to each subject, such that Group 1 panelists received the active tablets, and Group 2 received the placebo tablets. Subject group designations were determined in accordance with a computer-generated randomization code. Treatment designation/group assignment remained consistent throughout the study (FIGS. 5-6).

Each subject was provided with a designated test material, detailed study instructions and a new Daily Diary in which to record daily times of supplement use, daily application of the Cetaphil® Daily Facial Moisturizer SPF 15, and any suggestive comments pertaining to supplement usage.

The printed study instructions detailed study procedures for each visit and the appointment dates and times of the return visit(s) to Clinical Research Laboratories, Inc. Subjects were instructed to continue the use of the provided glycerin soap, twice daily, as well as the use of the Cetaphil® Daily Facial Moisturizer SPF 15, once per day.

Each subject was contacted, via telephone, by a CRL Technician for a Week 4 compliance check. After 8 weeks of ingesting the designated oral supplement, subjects reported to the CRL testing facility and each panelist acclimated to ambient temperature and humidity for a period of 30 minutes. Following acclimation, a dermal evaluation of the face of every subject was performed by a trained CRL Technician. Cutometer readings were taken. These procedures and evaluations were performed and recorded, as previously explained for the baseline study interval.

Subjects reported to Clinical Research Laboratories, Inc. following 12 weeks of supplement use and each subject acclimated to ambient temperature and humidity for a period of 30 minutes. Blood was drawn from each subject and the forearm used for blood collection was recorded on a case report form. A final urine specimen was obtained from each panelist. A dermal evaluation of the face was performed by a trained CRL Technician, for the presence of erythema, edema and dryness. Cutometer readings were captured from the cheekbone region below the eye on the same side of the face. All measurements were appropriately recorded.

At Week 12, all subjects completed a final questionnaire and unused portions of test materials and Daily Diaries were returned.

Statistical Methods

The primary efficacy parameters yielding significant results for this study are Cutometer measurements and consumer perception questionnaires.

One-way ANOVA tests (repeat-measurement) were applied to each group to determine if there were differences between baseline and Week 8, and baseline and Week 12 for all the parameters. If overall F-test was significant, Tukey's multiple comparison test was further applied to determine where the significant differences exist. The ANOVA test uses the F-test to determine whether there exists a significant difference among means of treatments or time intervals. When the F test rejects the null hypothesis, it is usually necessary to undertake a thorough analysis of the nature of the factor-level effects. Tukey test is a multiple comparison procedure. This is the method which examines or compares more than one pair of means or proportions at the same time but controls the overall significance level to be the same as that which is specified for a single pair comparison.

The comparisons between Group 1 (subjects assigned to the invention test material supplement) and Group 2 (subjects assigned to the placebo test material supplement) were based on percent changes from baseline at each time interval (Week 8 and Week 12). Two-sample t-tests were applied to determine if significant differences exist between Group 1 and Group 2. (FIGS. 8A-8D)

Two-tailed p-values of 0.05 or less was the criteria for significance, corresponding to a confidence level of 95%. All statistical computations were performed using Microsoft Excel or SAS® Statistical Analysis Software.

Results

Twenty subjects completed the study. One subject (#7) discontinued study participation for reasons unrelated to the test material.

Adverse Event

On Nov. 20, 2006, subject #6 (assigned to the placebo product) reported that on Nov. 17, 2006, following approximately 9 weeks of ingesting the placebo tablets, she noticed a red rash and hive-like bumps in the cheek area on both sides of her face and on her upper chest. The subject also reported that she experienced itching of these areas. On Nov. 20, 2006, upon examination by a CRL Certified Dermatologist, the subject was diagnosed with poison ivy. Subject #6 continued study participation. The Investigator determined that this adverse event of moderate severity was absolutely not related to the use of the test material. Follow-up telephone calls were made by a CRL Technician, and the information from each conversation was documented as follows: On Nov. 22, 2006, the subject reported that the hives had disappeared and the facial redness was diminishing.

On Nov. 27, 2006, subject #6 indicated that the rash was drying and nearly all of the redness was gone. On Dec. 8, 2006, the subject reported that the poison was gone and the adverse facial skin condition had completely resolved.

Instrumental Measurements, Dermal Evaluations and Questionnaire Responses

For both groups of subjects, FIGS. 7A-D summarize the Cutometer measurements for each panelist at each designated study interval. Table VI lists the statistical variables determined for comparisons of the differences between Week 8 and Week 12 measurements to baseline. For each subject, Table VII lists the baseline, Week 8 and Week 12 dermal evaluation scores for the presence of erythema, edema and dryness. Table VIII lists the questionnaire data for the screening questionnaire [combining both groups of subjects] based on percentages. Tables IX and X list the questionnaire data for the baseline and Week 12 (final) consumer perception questionnaires for Group 1 (subjects assigned to the active tablets) and for Group 2 (subjects assigned to the placebo tablets) based on percentages. Open-ended questions are also included in these questionnaire tables.

CONCLUSION

For each subject, study procedures included blood and urine analyses, sitting vital signs, a pregnancy test (with the exception of pre-menopausal panelists), Cutometer measurements and consumer perception questionnaires.

Blood Analysis

For each subject, a blood analysis was performed at the baseline and Week 12 study intervals, as indicated above. No clinically significant findings were determined at Week 12 relative to that which was revealed at baseline.

Urine Analysis

A urine specimen was obtained from each subject at baseline and at the Week 12 study interval, as specified above. No clinically significant findings were determined at Week 12 relative to that which was revealed at baseline.

Efficacy Evaluations

As assessed by the Cutometer parameter Ur/Ue, statistically significant differences existed between baseline and Week 12 for Group 1 subjects (assigned to the raw ingredient test material supplement, 10853LLA). The Cutometer parameter Ur/Ue describes skin elasticity as it relates to stretching and contracting. Seventy percent of Group 1 subjects showed an improvement in Cutometer parameter Ur/Ue. Relative to baseline, this significant increase in parameter Ur/Ue is equivalent to a 29% improvement at Week 12, suggesting that skin elasticity and distensibility improved for Group 1 subjects who ingested 10853LLA, the invention supplement. FIGS. 7A-8D summarize the statistical analysis of study results. FIG. 7D show a statistically significant improvement of Ur/Ue from baseline to week 12 (p=0.0109)

Questionnaire responses which were analyzed via Z-score analysis consisted of question numbers 10 through 15 in the Week 12 (Final) questionnaire. Favorable consumer perception questionnaire responses of the study population at Week 12 (final visit), which were applicable to Z-score analysis, as listed below, were measured with statistical significance (Z-scores greater than or equal to the absolute value of 1.96) in questionnaires completed by each subject.

A significant proportion of the Group I study population assigned to 10853LLA, the active tablets, perceived improvements following 12 weeks of supplement use and subjects responded favorably with regard to the following treatment effects:

Approximately 85% of subjects agreed that after using the product for 12 weeks, they experienced muscle and/or joint pain less frequently.

Approximately 85% of subjects agreed that after using the product for 12 weeks, the overall pain has been less intense.

Approximately 90% of subjects agreed that after using the product for 12 weeks, the pain did not last as long.

Approximately 85% of subjects agreed that the product had a positive effect on their joint and/or muscle pain. The detailed statistical results are shown in FIGS. 8A-B.

For the Group 2 study population assigned to 10853LLB, the placebo tablets, no favorable responses were reported following 12 weeks of supplement use. The results are shown in FIGS. 9A-B.

STUDY REFERENCES

Basel, Courage and Clarys, Handbook of Non-Invasive Methods and the Skin, Serup and Jemec, eds. 1995.

Blichman and Serup, Acta Derm Venereol, 1988.

Cua, Maibach and Wilhelm, Dermatologica Research, 1990.

Dobrev, Sixth Congress of Dermatology and Venerology, Pleve, Bulgaria, May 11-13, 1995.

Elsner, Eighth International Symposium "Bioengineering and the skin," Stresa/Italia, June 1990.

Frankowski, Chen and Huth, Photonics West Annual Symposium, Electronics Imaging 2000, San Jose, Jan. 23-28, 2000.

Fiorentini, Becheroni, Iorio. Int. J. Cosmet. Sci. 26-29, 1988.

Friedman, Skover, Payonk and Geronemus, Seminars in Cutaneous Medicine and Surger, 200, 21 (4):266-273.

Krushe and Worre, Archives of Dermatologica Research. 287-293, 1995.

Morganti, Randazzo and Cardillo. Appl. Cosmet. 10-12, 1986.

Randeau, Kurdian, Sirvent, Closs and Girard, Cosmetics and Toiletries Manufacture Worldwide 2002.

Simon, Arzliche Kosmetologie, 256-259, 1984.

All references mentioned above are expressly are expressly incorporated by reference into the instant application.

Method for Monocyte Activation Assay

Monocyte activation assay was used to evaluate immunostimulatory activity. The THP-1 human monocyte cell line was transfected with a luciferase reporter gene construct containing two copies of the NF-kappa B motif for HIV/IgK as described previously. This monocyte activation assay is an example of an in vitro test system that can be used for bioactivity based standardization of *Aloe vera* extracts and product material.

Method for Toll-Like Receptor 2 (TLR2) Expression Vector Experiment

HEK 293 cells were cultured in DMEM/F12 medium supplemented with fetal bovine serum (10%) and 1% penicillin-streptomycin at 37° C., under 5% $CO_2$. Actively growing cells were transiently transfected with the appropriate plasmid(s) using electroporation (at 150 V and one 70-ms pulse). Following electroporation, cells were plated at a density of $5\times10^4$ cells in 200 µl/well of culture medium. After 48 hours, agents to be tested were added to transfected cells. Six hours after addition of samples, cells were harvested and luciferase activity measured. The NF-kappa B plasmid construct (pBIIXLUC) contained two copies of NF-kappa B motif from HIV/IgK. Plasmids co-expressing human CD14 and human TLR2 (pDUO-hCD14/TLR2) were purchased from InvivoGen. Zymosan was purchased from Sigma, *Staphylococcus aureus* peptidoglycan from Fluka and ultra pure *Salmonella minnesota* LPS from List Biological Laboratories, Inc.

AloeEx Activates NF-Kappa B In Vitro Through a TLR2-Dependent Process.

Figure 10B:
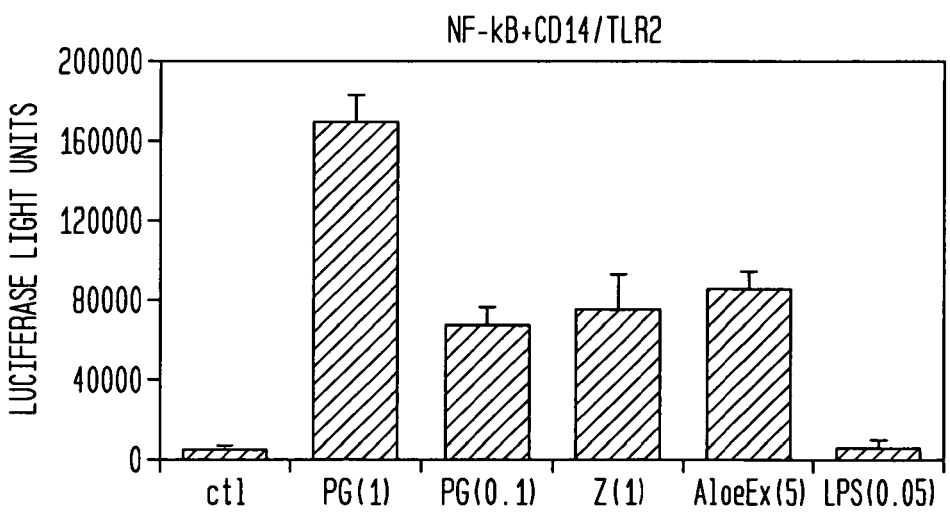

FIGS. 10A-10B depict that AloeEx (batch 2-5-05) acts through TLR2. HEK 293 cells (cell line with minimal TLR expression) were transiently transfected with a luciferase reporter gene construct containing two binding sites for NF-kappa B, alone (FIG. 10A), or in combination with the pDUO-hCD14/TLR2 expression plasmid (FIG. 10B). The pDUO-hCD14/TLR2 expression plasmid expresses proteins supporting TLR2- (CD14 and TLR2) dependent NF-kappa B activation. Forty-eight hours after transfection, cells were treated with either AloeEx TLR2 agonists peptidoglycan (PG) or zymosan (Z), or TLR4 agonist ultrapure *S. minnesota* lipo-polysaccharide (LPS) at the indicated concentrations (µg/ml). Luciferase activity was determined 6 hours after addition of agents.

Neither the TLR2 specific (peptidoglycan or zymosan) or TLR4 specific (ultrapure LPS) ligands nor AloeEx activated NF-kappa B-dependent luciferase expression in HEK 293 cells transfected with the reporter plasmid alone (FIG. 10A). AloeEx activated NF-kappa B in cells supporting TLR2-dependent (expressing CD12 and TLR2) activation (FIG. 10B). Peptidoglycan and zymosan also activated NF-kappa B in cells expressing TLR2 and CD14 as compared with ultrapure LPS which did not.

Presence of ALPs and ALP in AloeEx

The inventors have demonstrated that AloeEx contains bacterial LPS and bacterial lipo-proteins that are most likely derived from microorganisms that are associated with *Aloe vera*. The presence of these bacterial components in AloeEx are believed to contribute to the therapeutic properties of products derived from AloeEx.

Figure 11:
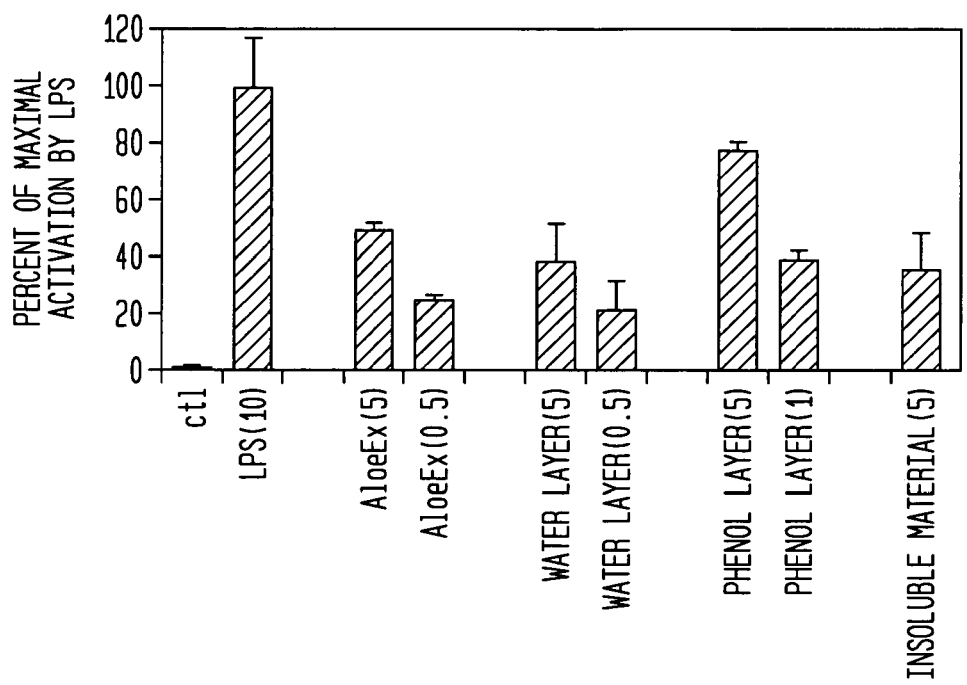
FIG. 11—depicts the reponse of THP-1 cells to AloeEx (batch 056) and AloeEx crude fractions.

AloeEx was extracted with 90% aqueous phenol:water (1:1) at 70° C. Upon cooling the extract and subsequent centrifugation two layers were formed (water and phenol) and a pellet of insoluble material. The water layer contains ALPS. Due to the non-polar lipid moiety on lipo-proteins, the phenol layer contain the ALPs. Using this procedure, AloeEx (batch 056) was separated into a water layer fraction, a phenol layer fraction and insoluble material. The water layer fraction was freeze-dried (8.9% yield). Material in the phenol layer was precipitated by addition of 2 volumes of ether:acetone (1:5) and 4 volumes of ethyl acetate. The phenol layer precipitate was washed extensively with ethyl acetate and isopropanol and then dried at 60° C. (45% yield). The original AloeEx material, water layer fraction, phenol layer fraction and insoluble material were all tested in the monocyte assay (FIG. 11). Twenty-fours hours following transfection with the NF-kappa B luciferase reporter plasmid, cells were treated with the indicated sample for 4 hours (concentrations in µg/ml). Luciferase activity was determined and is reported as a percent of maximal light output from LPS-treated cells. Both the water layer and phenol layers exhibited substantial monocyte activation believed to be due to bacterial ALPS and ALP, respectively. The insoluble material was also active as indicated by its ability to enhance NF-kappa B activation by 35% when tested at 5 µg/ml.

Characterization of ALPs in AloeEx Phenol Layer Fraction

The phenol layer fraction material was extracted three times with 4% sodium dodecyl sulfate (SDS) (26 mg/ml) at 100° C. for 30 minutes. SDS insoluble material was removed by centrifugation and when tested in the monocyte assay contained only about 1-2% of the total activity present in the original phenol layer fraction.

The SDS extract of the phenol layer fraction was incubated with 0.1 mg/ml (3.9 units/ml) proteinase K from *Tritirachium album* (Sigma) in 50 mM TRIS (pH 7.5), 5 mM β-mercaptoethanol, and 5 mM $CaCl_2$ for 2 hours at 50° C. The digest was then heated at 98° C. for 10 minutes. A control sample, without proteinase K, was run under identical conditions. For SDS polyacrylamide gel analysis, extract (proteinase K treated and untreated) was mixed with 1 volume of Tris-Tricine sample buffer (Bio-Rad) and loaded in nonadjacent lanes of a 16.5% Tris-Tricine precast gel (Ready Gel, Bio-Rad). The amount of sample loaded represented the SDS extractable material present in 130 µg of AloeEx phenol layer fraction. Wide molecular weight range protein marker (Sigma) was run in the gel. Individual gel lanes were cut into 12 equal sections (0.5 cm/section) and extracted with 150 µl of 1.5% octylglucoside, 2.5 mM TRIS (pH 7.5), 5 mM $CaCl_2$ at 95° C. for 5 minutes. Supernatants of samples were collected and evaluated for activity in the monocyte activation assay.

Figure 12:
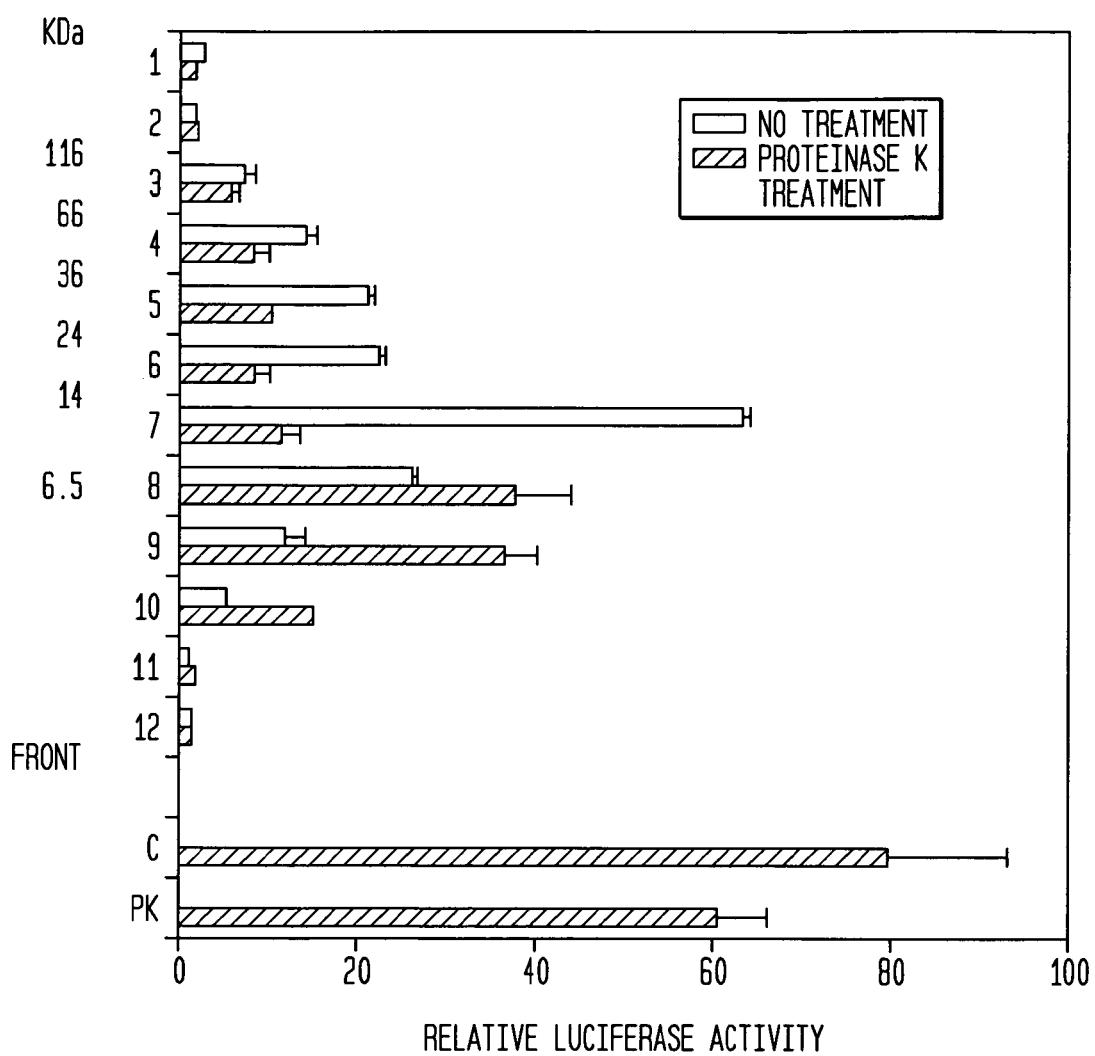
FIG. 12—depicts proteinase K digestion and SDS polyacrylamide gel analysis of 4% SDS extract of AloeEx phenol layer fraction.

FIG. 12 indicates that protein does not appear to be directly responsible for the activation of the monocytes by AloeEx phenol layer fraction, but rather that protein is part of the molecule that is responsible for this activity. This is indicated by the reduction in the apparent size of the active compounds following proteinase K treatment as determined by fractionation on an SDS-polyacrylamide gel. Following proteinase K treatment there was a substantial reduction in activity for the region between 66 and 6.5 kDa, while there was an increase in activity for the region between 6.5 kDa and the gel front. This result is similar to those obtained with bacterial lipoproteins in that proteinase K digestion does not reduce the activity of the lipoproteins (i.e. the protein component of the lipo-protein is not necessary for monocyte activation) but proteinase K treatment does reduce the size of the lipo-proteins when fractionated on an SDS-polyacrylamide gel. The black bars labeled "C" and "PK" in FIG. 12 represent the activity of the untreated and proteinase K treated AloeEx phenol layer fraction, respectively, before fractionation on the gel.

To determine sensitivity of the 4% SDS extract of the AloeEx phenol layer fraction to lipo-protein lipase, the SDS was removed using SDS-out reagent (Pierce) in the presence of 0.88% octylglucoside. The sample was then adjusted to a final concentration of 10 µM AEBSF protease inhibitor cocktail solution (Sigma) and 0.2% BSA (Sigma, No. A-9418). The sample was incubated at 37° C. for 16 hours with 39,600 units/ml (1 mg/ml) of lipo-protein lipase from *Pseudomonas* species (Sigma No. L9656). Control samples (without lipo-protein lipase) were run under identical conditions. Activity of lipo-protein lipase treated and untreated samples were evaluated using the monocyte activation assay.

Figure 13:
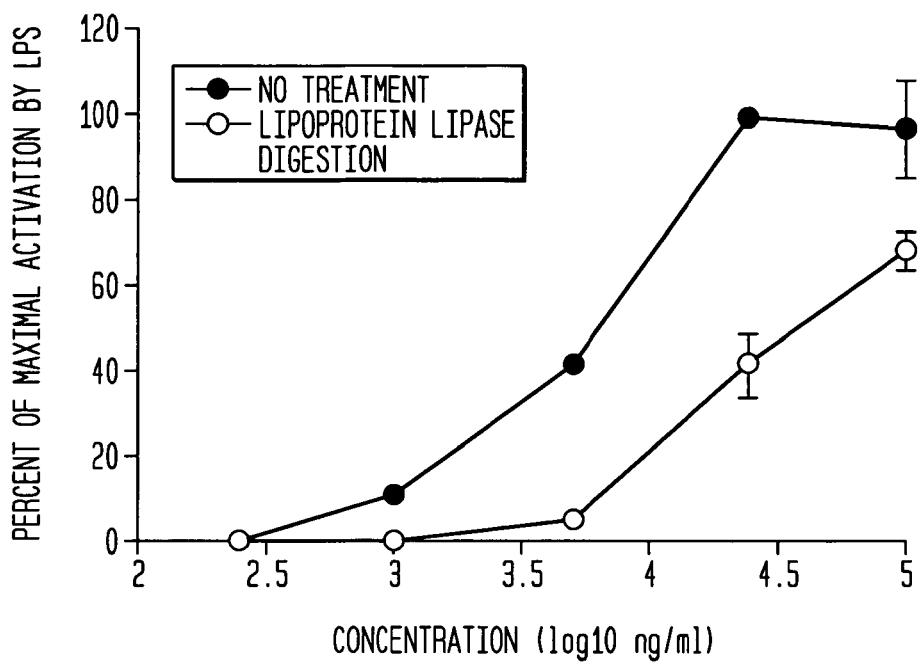
FIG. 13—depicts lipoprotein lipase digestion of 4% SDS extract of AloeEx phenol layer fraction.

The results as depicted in FIG. 13 show that the activity present in the 4% SDS extract of AloeEx phenol layer fraction is completely abrogated by treatment with lipo-protein lipase. This result together with the results presented in. FIG. 12 confirms that the activity in the AloeEx phenol layer fraction is due to ALPs. This procedure demonstrated that AloeEx contains ALPs that are believed to be derived from microorganisms that are associated with *Aloe vera*. The presence of this bacterial component, combined with other components in AloeEx, are believed to significantly contribute to the therapeutic properties of this product.

Characterization of alps in AloeEx

The following summarizes the amount of ALPS present in AloeEx (batch 056) and the two fractions derived from this material (water layer fraction and phenol layer fraction).

| | |
|---|---|
| AloeEx (batch 056) | 625-6250 EU/mg |
| AloeEx Water Layer Fraction | 62,500-625,000 EU/mg |
| AloeEx Phenol Layer Fraction | <4.8 EU/mg |

The amount of ALPS was estimated using Pyrosate LAL assay kit (Associates of Cape Cod Inc) according to manufacture's instruction. As expected, the water layer fraction contained essentially all of the ALPS present in AloeEx, as compared to the phenol layer fraction. This data demonstrated that AloeEx contains ALPS that is believed to be derived from microorganisms that are associated with *Aloe vera*. The presence of this bacterial component combined with other components in AloeEx are believed to contribute to the therapeutic properties of this product.

The Rind and Mucilage Contain the Majority of the Monocyte Activating Components in *Aloe vera*

Figure 14:
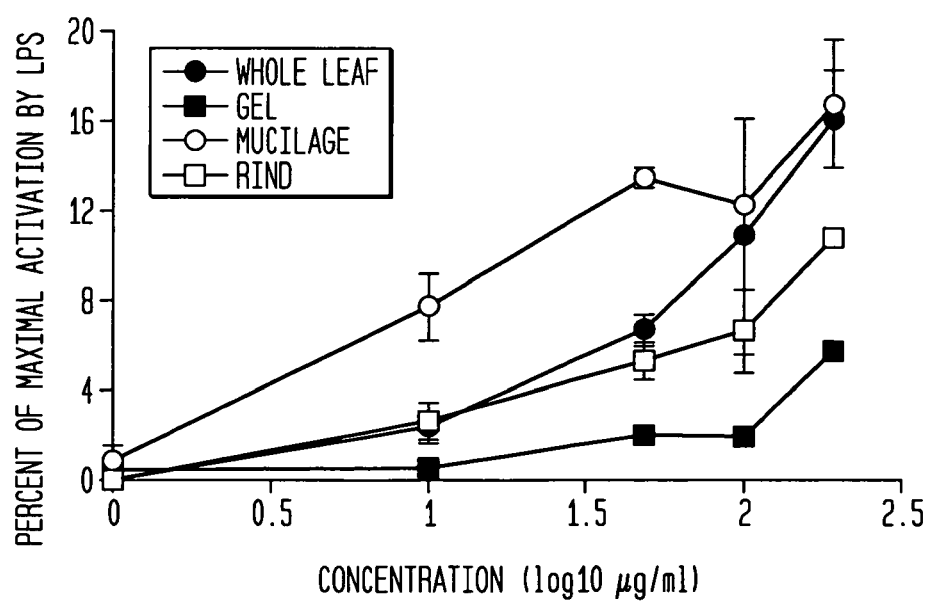
FIG. 14—depicts the reponse of THP-1 cells to different *Aloe vera* leaf parts.

The *Aloe vera* leaf can be divided into three basic structural parts: the gel, the outer rind and the mucilage (the layer between the gel and the outer rind). An experiment was conducted to determine which part of the *Aloe* leaf contained the highest level of monocyte activating components. From one *Aloe vera* leaf, the gel was carefully cut-out by passing a knife parallel to the inner rind surface. After removal of the gel, the leaf was scraped over the edge of a vial to collect the mucilage part and to separate it from the outer rind. All three components and a section of the whole leaf *Aloe* were freeze-dried and ground to a fine powder. Each sample was then extensively extracted with methanol to remove non-polar substances, such as anthraquinones, that have an inhibitory effect in the monocyte activation assay. Samples with non-polar substances removed were prepared as a fine suspension in water. Twenty-fours hours following transfection with the NF-kappa B luciferase reporter plasmid, THP-1 cells were treated with the prepared samples for 4 hours. Luciferase activity was determined and is reported as a percent of maximal light output from ELPS-treated cells. FIG. 14 depicts the response of the different *Aloe vera* leaf parts and that of the whole leaf material. This data suggests that the mucilage layer and outer rind contain the majority of the monocyte activating components in the *Aloe* leaf. In this experiment, the percent that each leaf part comprises of the total dry weight of the *Aloe* leaf was: gel (8.7%), mucilage layer (6.2%) and rind (85.1%).

Since the outer rind and mucilage layer contain the majority of the monocyte activating components, and these parts also comprise the majority of the dry solids in the *Aloe* leaf, the inventors conclude that the outer rind and mucilage layer are of commercial interest. Typically, the outer rind is discarded as a waste product after the gel has been removed or after the whole *Aloe* leaf has been processed to create *Aloe* juice. Another waste product is *Aloe* pups (small *Aloe* plants that grow off of the larger plants). Since the *Aloe* pups contain mostly rind with very little gel and are considered of little commercial value. The rind and *Aloe* pups waste products can be processed to produce for example, dietary supplements that enhance immune function. The dried rind could be ground to a powder and processed to remove anthraquinones. This material could be further processed by extraction to produce crude extracts and purified fractions. The objective of the crude extracts and purified fractions would be to concentrate the amount of AloeEx and/or microorganisms and microorganism fragments/components associated with *Aloe vera*.

Monocyte activating components in AloeEx are Extractable and Soluble in Detergent For development of various products (e.g. for cosmetics) it may be desirable to solublize the immune enhancing components in AloeEx material. The immune enhancing components would include Aloeride polysaccharide, ALPs and ALPSs derived from microorganisms that are associated with *Aloe vera*. As previously described, a significant portion of the immune enhancing components of AloeEx material can be fractionated into a water layer fraction and phenol layer fraction. The immune enhancing activity present in the phenol layer fraction (ALPs) can be completely extracted/solubilized with 4% SDS at 100° C. The immune enhancing activity present in the water layer (ALPS and Aloeride polysaccharides) is water soluble and also SDS soluble.

Extraction of AloeEx with SDS represents a potential method to solublize a significant portion of the immune enhancing components present in this material. The data suggest that other known detergents (including those that are more compatible with product formulation) could also be potentially useful in extraction/solublization of the immune enhancing components in AloeEx material. This method of detergent extraction could also be used to solubilize the monocyte activating components (i.e. Aloeride polysaccharide and microorganism components associated with *Aloe vera*) from raw materials such as whole leaf, rind, *Aloe* pups, etc.

Method for Producing an Extract by Isolation of Microorganisms and Microorganism Components/Fragments Associated with *Aloe vera*

As demonstrated, bacterial products from microorganisms associated with *Aloe vera* are responsible for a significant portion of the immune enhancing properties of AloeEx. It is shown that AloeEx accounts for a majority of the in vitro monocyte/macrophage activation potential of *Aloe vera*. Therefore, it is believed that bacterial products from microorganisms are responsible for a significant portion of the immune enhancing properties of *Aloe vera*.

Extracts that concentrate the amount of microorganisms and/or microorganism components/fragments associated with *Aloe vera* can be prepared from crude *Aloe* material and/or *Aloe vera* raw material, including waste material (e.g. leftover rinds, *Aloe* pups, etc.). Crude extracts can be processed to create purified fractions by extracting the bacterial lipo-proteins and/or other bacterial components using a solvent. These fractions would contain enhanced levels of bacterial components associated with *Aloe vera*. Solvents which may be used to prepare a purified fraction include detergents such as SDS, water, water miscible solvents such as alcohol, and combinations of these solvents or other solvents well known in the art.

The following procedure could be used to prepare an extract that concentrates the microorganisms and/or microorganism components/fragments associated with *Aloe vera*. *Aloe vera* raw material (gel, whole leaf, rind, pups, etc.) can be liquified using methods known in the art. The liquid can be subjected to coarse filtration to remove fibrous material. A food-grade flocculant (clarifier or similar substance) can be added to the liquified *Aloe* to create aggregates of particles (bacterial, other microorganisms, microorganism fragments/components). These aggregated particles could then be separated from the remaining liquid using methods known in the art. Such methods would include centrifugation, filtration, settling followed by decanting, filtering aggregates out of the liquid using a net, etc. The final collected material can be also processed to remove anthraquinones, if present, using a technique such as washing/extracting with alcohol. If desired, the resulting material can be dried.

Method for Producing a Standardized *Aloe vera* Product

Biological and chemical standardization represent two methods that can be used to standardize *Aloe vera* products that contain the immune enhancing agents described in the present invention. Both methods can be used for standardizing either extract material or the raw material. The purpose of standardization is to ensure that each batch of product material contains the same level of active component(s).

In one method a bioactivity standardized *Aloe vera* product containing an effective amount of immunostimulatory activity is prepared. In this method, *Aloe vera* product material is tested in vitro for activation of immune cells and the bioactivity is then compared to a standard preparation immunostimulatory value to determine a standardized activity value of the product. An example of an in vitro test system is the monocyte activation assay previously described. Bioactivity based standardization of product material is important when the chemical content of the active components do not correlate with biological activity due to unknown structure-activity relationships and/or complex interactions between multiple actives. Under such circumstances, the amount of active substances is not sufficient to reflect the potency of the product material and standardization through the use of a biological assay is desirable. Bioactivity standardization has been used by the pharmaceutical industry for biologics such as insulin and cytokines.

In another method a chemically standardized *Aloe vera* product containing an effective amount of immunostimulatory lipo-proteins originating from microorganisms associated with *Aloe vera* is prepared. A chemical marker which may be used for standardization is 2,3-dihydroxypropyl cysteine. This modified cysteine amino acid is thought to be unique to lipo-proteins that are immunostimulatory from prokaryotic organisms. In this method, *Aloe vera* product material is tested for the amount of 2,3-dihydroxypropyl cysteine and then compared to the amount of 2,3-dihydroxypropyl cysteine in a standard preparation to determine a standardized value of the product.

In certain embodiments a food grade flocculent, clarifier or coagulant may be used to form microorganism aggregates. Examples include, but are not limited to, for example, alum, aluminium chlorohydrate, aluminum sulfate, calcium oxide, iron(III) chloride, iron(II) sulfate, polyacrylamide, sodium aluminate, sodium silicate and combinations thereof. Natural products which can also be used as flocculants include Chitosan, *Moringa oleifera* seeds, Papain, species of *Strychnos* (seeds) Isinglass and combinations thereof. Other such materials are well known to those skilled in the art.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of making an immunostimulatory composition said method comprising:
    mixing an immunostimulatory *Aloe vera*-derived mixture and an *Aloe vera*-derived material to produce the immunostimulatory composition,
    wherein the amount of the *Aloe vera*-derived material ranges from 10 wt % to about 90 wt % relative to the total amount of the immunostimulatory *Aloe vera*-derived mixture and the *Aloe vera*-derived material,
    wherein the immunostimulatory *Aloe vera*-derived mixture comprises at least one *Aloe vera*-derived lipo-polysaccharide, at least one *Aloe vera*-derived polysaccharide, and at least one *Aloe vera*-derived lipo-protein, the immunostimulatory *Aloe vera*-derived mixture, at a concentration of about 250 µg/mL or less, exhibits an immunostimulatory activity of at least 50% of a maximal NF-kappa Beta directed luciferase expression by *Escherichia coli* bacterial lipo-polysaccharide (ELPS) at a concentration of about 10 µg/mL, and the immunostimulatory activity is measured by NF-kappa Beta directed luciferase expression in THP-1 monocytes, and
    wherein the *Aloe vera*-derived material is selected from the group consisting of Aloe vera gel concentrated at 1×, *Aloe vera* gel concentrated at 10×, *Aloe vera* gel concentrated at 200×, *Aloe vera* whole leaf spray dried powder concentrated at 100×, *Aloe vera* whole leaf decolorized liquid, acemannan, and *Aloe vera* mucilaginous polysaccharide.

2. The method of claim 1, wherein the *Aloe vera*-derived polysaccharide comprises glucose in molar amount ranging from about 25% to about 70%, rhamnose in a molar amount ranging from about 0.5% to about 35%, galactose in a molar amount ranging from about 5% to about 30%, mannose in a molar amount ranging from about 3% to about 25%, and arabinose in a molar amount ranging from about 0% and about 15%, based on the total molar amount of the *Aloe vera*-derived polysaccharide, and
    wherein the *Aloe vera*-derived polysaccharide has a molecular weight greater than about 2,000,000 Daltons.

3. The method of claim 2, wherein the immunostimulatory *Aloe vera*-derived mixture comprises between 0.01% and 50% by weight of the *Aloe vera*-derived polysaccharide and between 0.0001% and 10% by weight of the combination of the *Aloe vera*-derived lipo-protein and *Aloe vera*-derived lipo-polysaccharide.

4. The method of claim 3, wherein the immunostimulatory *Aloe vera*-derived mixture comprises between 1% and 20% of the *Aloe vera*-derived polysaccharide.

5. The method of claim 3, wherein the immunostimulatory *Aloe vera*-derived mixture comprises between 1% and 15% by weight of the *Aloe vera*-derived polysaccharide.

6. The method of claim 3, wherein the immunostimulatory *Aloe vera*-derived mixture comprises between 10-15% by weight of the *Aloe vera*-derived polysaccharide.

7. The method of claim 1, wherein the *Aloe vera*-derived lipo-protein, *Aloe vera*-derived lipo-polysaccharide and/or *Aloe vera*-derived polysaccharide are extracted from *Aloe vera*.

8. The method of claim 7, wherein the *Aloe vera* includes at least one of *Aloe vera* rind, *Aloe vera* mucilage, *Aloe vera* gel, or whole leaf *Aloe vera*.

9. The method of claim 1, further comprising mixing the immunostimulatory composition with a pharmaceutical carrier or excipient.

10. The method of claim 1, wherein the *Aloe vera*-derived material is an immunostimulatory *Aloe vera*-derived material.

11. The method of claim 1, wherein the *Aloe vera*-derived material is *Aloe vera* gel concentrated at 200× and wherein the *Aloe vera* gel concentrated at 200× is present in the composition in an amount which is about 80% by weight relative to the total amount of the material and the immunostimulatory *Aloe vera*-derived mixture.

12. The method of claim 1, wherein the *Aloe vera*-derived lipo-protein, *Aloe vera*-derived lipo-polysaccharide and/or *Aloe vera*-derived polysaccharide are synthetic.

13. The method of claim 1, wherein the *Aloe vera*-derived material is a non-immunostimulatory *Aloe vera*-derived material.

14. The method of claim 1, wherein the mixing step further comprises:
    homogenizing the immunostimulatory *Aloe vera*-derived mixture and the *Aloe vera*-derived material in a solvent to produce the immunostimulatory composition.

15. The method of claim 14, wherein said immunostimulatory composition is selected from the group consisting of a homogenous solution, homogeneous suspension, homogenous dispersion, and homogenous emulsion.

16. The method of claim 1, wherein the immunostimulatory *Aloe vera*-derived mixture exhibits an immunostimulatory activity of at least 50% of a maximal NF-kappa Beta directed luciferase expression by *Escherichia coli* bacterial lipo-polysaccharide (ELPS) at a concentration of about 10 µg/mL, and the immunostimulatory activity is measured by NF-kappa Beta directed luciferase expression in THP-1 monocytes at a concentration of about 5 µg/mL to about 250 µg/mL.

17. The method of claim 1, wherein the immunostimulatory *Aloe vera*-derived mixture is insoluble in water.

18. An immunostimulatory composition comprising:
    an effective amount of an immunostimulatory *Aloe vera*-derived mixture and an *Aloe vera*-derived material,
    wherein the immunostimulatory *Aloe vera* -derived mixture comprises at least one *Aloe vera*-derived lipo-polysaccharide, at least one *Aloe vera*-derived polysaccharide and at least one *Aloe vera*-derived lipo-protein,
    wherein the immunostimulatory *Aloe vera*-derived mixture exhibits an immunostimulatory activity of at least 50% of a maximal NF-kappa Beta directed luciferase expression by *Escherichia coli* bacterial lipo-polysaccharide (ELPS) at a concentration of about 10 µg/mL, and the immunostimulatory activity is measured by NF-kappa Beta directed luciferase expression in THP-1 monocytes at a concentration of about 250 µg/mL or less,
    wherein the *Aloe vera*-derived material is selected from the group consisting of *Aloe vera* gel concentrated at 1×, *Aloe vera* gel concentrated at 10×, *Aloe vera* gel concentrated at 200×, *Aloe vera* whole leaf spray dried powder concentrated at 100×, *Aloe vera* whole leaf decolorized liquid, acemannan, and *Aloe vera* mucilaginous polysaccharide, wherein the amount of the *Aloe vera*-derived material ranges from 10 wt % to about 90 wt % relative to the total amount of the immunostimulatory *Aloe vera*-derived mixture and the *Aloe vera*-derived material, and wherein the composition is selected from the group consisting of an emulsion, a microemulsion, a topical cream, a capsule, a tablet, a pill, and a dragee.

19. The immunostimulatory composition of claim 18, wherein the *Aloe vera*-derived polysaccharide comprises glucose in molar amount ranging from about 25% to about 70%, rhamnose in a molar amount ranging from about 0.5% to about 35%, galactose in a molar amount ranging from about 5% to about 30%, mannose in a molar amount ranging from about 3% to about 25%, and arabinose in a molar amount ranging from about 0% and about 15%, based on the total molar amount of the *Aloe vera*-derived polysaccharide, and wherein the *Aloe vera*-derived polysaccharide has a molecular weight greater than about 2,000,000 Daltons.

20. The immunostimulatory composition of claim 19, wherein the immunostimulatory *Aloe vera*-derived mixture comprises between 0.01% and 50% by weight of the *Aloe vera*-derived polysaccharide and between 0.0001% and 10% by weight of the combination of the *Aloe vera*-derived lipo-protein and *Aloe vera*-derived lipo-polysaccharide.

21. The immunostimulatory composition of claim 20, wherein the immunostimulatory *Aloe vera*-derived mixture comprises between 1% and 20% by weight of the *Aloe vera*-derived polysaccharide.

22. The immunostimulatory composition of claim 20, wherein the immunostimulatory *Aloe vera*-derived mixture comprises between 1% and 15% by weight of the *Aloe vera*-derived polysaccharide.

23. The immunostimulatory of claim 20, wherein the immunostimulatory *Aloe vera*-derived mixture comprises between 10-15% by weight of the *Aloe vera*-derived polysaccharide.

24. The immunostimulatory composition of claim 18, wherein the immunostimulatory *Aloe vera*-derived mixture is obtained from *Aloe vera*, wherein the *Aloe vera* includes at least one of *Aloe vera* rind, *Aloe vera* mucilage, *Aloe vera* gel, or whole leaf *Aloe vera*.

25. The composition of claim 18, further comprising a pharmaceutical carrier or excipient.

26. The immunostimulatory composition of claim 18, wherein the *Aloe vera*-derived material is selected from the group consisting of an immunostimulatory *Aloe vera*-derived material and a non-immunostimulatory *Aloe vera*-derived material.

27. The immunostimulatory composition of claim 18, wherein the *Aloe vera*-derived material is *Aloe vera* gel concentrated at 200× and wherein the *Aloe vera* gel concentrated at 200× is present in the composition in an amount of about 80% by weight relative to the total amount of the *Aloe vera*-derived material and the immunostimulatory *Aloe vera*-derived mixture.

28. The immunostimulatory composition of claim 18, wherein the total amount of the immunostimulatory *Aloe vera*-derived mixture and the *Aloe vera*-derived material is present in the immunostimulatory composition in an amount between 0.05% and 5% by weight of the total weight of the immunostimulatory composition.

29. The immunostimulatory composition of claim 28, wherein the total amount of the immunostimulatory *Aloe vera*-derived mixture and the *Aloe vera*-derived material is 0.5% by weight of the total weight of the composition.

30. A method of improving the appearance, texture, firmness and/or elasticity of skin and/or for providing accelerated growth of new skin cells in a subject in need thereof comprising administering to said subject an effective amount of the immunostimulatory composition of claim 27.

31. The composition of claim 27, further comprising a pharmaceutical carrier or excipient.

32. The immunostimulatory composition of claim 18, wherein the immunostimulatory *Aloe vera*-derived mixture exhibits an immunostimulatory activity of at least 50% of a maximal NF-kappa Beta directed luciferase expression by *Escherichia coli* bacterial lipo-polysaccharide (ELPS) at a concentration of about 10 μg/mL, and the immunostimulatory activity is measured by NF-kappa Beta directed luciferase expression in THP-1 monocytes at a concentration of about 5 μg/mL to about 250 μg/mL.

33. The immunostimulatory composition of claim 18, wherein the immunostimulatory *Aloe vera*-derived mixture is insoluble in water.

34. A method of treating muscle or joint pain in a subject in need thereof comprising administering to said subject an effective amount of the immunostimulatory composition of claim 18.

35. The method of claim 34, wherein the subject is a human being.

36. The method of claim 34, wherein the subject is an animal.

37. The method of claim 34, wherein the effective amount of the immunostimulatory composition is between 0.2 milligrams and 1 gram per day.

38. A method of improving the appearance, texture, firmness and/or elasticity of skin and/or for providing accelerated growth of new skin cells in a subject in need thereof comprising administering to said subject an effective amount of the immunostimulatory composition of claim 18.

39. The method of claim 38, wherein the subject is a human being.

40. The method of claim 38, wherein the subject is an animal.

41. The method of claim 38, wherein the effective amount of the immunostimulatory composition is between 0.0005 milligrams and 1 gram per day.

42. A method of treating muscle or joint pain in a subject in need thereof comprising administering to said subject an effective amount of the immunostimulatory composition of claim 27.

43. A method of treating muscle or joint pain in a subject in need thereof comprising administering to said subject an effective amount of the immunostimulatory composition of claim 31.

44. A method of improving the appearance, texture, firmness and/or elasticity of skin and/or for providing accelerated growth of new skin cells in a subject in need thereof comprising administering to said subject an effective amount of the immunostimulatory composition of claim 31.

45. An immunostimulatory composition, comprising:
an effective amount of an immunostimulatory *Aloe vera*-derived mixture, the immunostimulatory *Aloe vera*-derived mixture comprising at least one *Aloe vera*-derived lipo-polysaccharide, at least one *Aloe vera*-derived polysaccharide, and at least one *Aloe vera*-derived lipo-protein, wherein the immunostimulatory *Aloe vera*-derived mixture exhibits an immunostimulatory activity of at least 50% of a maximal NF-kappa Beta directed luciferase expression by *Escherichia coli* bacterial lipo-polysaccharide (ELPS) at a concentration of about 10 µg/mL, and the immunostimulatory activity is measured by NF-kappa Beta directed luciferase expression in THP-1 monocytes at a concentration of about 250 µg/mL or less, and wherein the compositionis selected from the group consisting of an emulsion, a microemulsion, a topical cream, a capsule, a tablet, a pill, and a dragee.

46. The immunostimulatory composition of claim 45, wherein the immunostimulatory *Aloe vera*-derived mixture is insoluble in water.

* * * * *